US009115205B2

(12) United States Patent
Dutta

(10) Patent No.: US 9,115,205 B2
(45) Date of Patent: Aug. 25, 2015

(54) PLASMODIUM FALCIPARUM CIRCUMSPOROZOITE VACCINE GENE OPTIMIZATION FOR SOLUBLE PROTEIN EXPRESSION

(75) Inventor: Sheetij Dutta, Silver Spring, MD (US)

(73) Assignee: The United States of America, as represented by the Secretary of the Army, Fort Detrick, MD (US)

( * ) Notice: Subject to any disclaimer, the term of this patent is extended or adjusted under 35 U.S.C. 154(b) by 0 days.

(21) Appl. No.: 13/880,227

(22) PCT Filed: Oct. 18, 2011

(86) PCT No.: PCT/US2011/056729

§ 371 (c)(1), (2), (4) Date: Jun. 11, 2013

(87) PCT Pub. No.: WO2012/154199

PCT Pub. Date: Nov. 15, 2012

(65) Prior Publication Data

US 2013/0259890 A1 Oct. 3, 2013

Related U.S. Application Data

(60) Provisional application No. 61/394,048, filed on Oct. 18, 2010.

(51) Int. Cl.

*A61K 39/00* (2006.01)
*A61K 39/02* (2006.01)
*C07K 14/445* (2006.01)
*A61K 39/015* (2006.01)

(52) U.S. Cl.

CPC ............ *C07K 14/445* (2013.01); *A61K 39/015* (2013.01); *A61K 2039/55566* (2013.01)

(58) Field of Classification Search

None

See application file for complete search history.

(56) References Cited

U.S. PATENT DOCUMENTS

| | | | |
|---|---|---|---|
| 6,482,607 | B1 | 11/2002 | Reymond |
| 7,438,916 | B2 | 10/2008 | Rathore |
| 2004/0067880 | A1 | 4/2004 | Kuo |
| 2006/0088547 | A1 | 4/2006 | Lanar et al. |
| 2006/0188527 | A1 | 8/2006 | Hoffman et al. |
| 2007/0041992 | A1 | 2/2007 | Frevert et al. |
| 2010/0137162 | A1 | 6/2010 | Retallack |
| 2010/0255075 | A1 | 10/2010 | Bergman-Leitner et al. |

FOREIGN PATENT DOCUMENTS

| | | |
|---|---|---|
| EP | 252588 | 1/1988 |
| WO | 8706939 | 11/1987 |
| WO | 9217204 | 10/1992 |
| WO | 2008027414 A2 | 3/2008 |
| WO | 2008086386 A2 | 7/2008 |
| WO | 2009091692 | 7/2009 |
| WO | 2011022522 | 2/2011 |

OTHER PUBLICATIONS

Mehlin et al. (Molecular and Biological Parasitology , vol. 148, pp. 144-160, 2006).*
Int'l Search Report and Written Opinion for PCT/US2011/56729 dated Oct. 2, 2012.
Organesyan, N., Bio-Rad Laboratores 2009: Bulletin 5772.
Kolodny et al. (Journal of Chromatography B: Biomedical Sciences and Applications, vol. 762, Issue 1, Oct. 5, 2001, p. 77-86).
Bell et al. (Vaccine 27 (2009) 1448-1453).
Caspers et al. (Molecular and Biochemical Parasilogy, 47(2):143-150 (1991)).
Ballou et al. (Lancet. vol. 329, Issue 8545, Jun. 6, 1987, pp. 1277-1281).
Folena-Wasserman et al. (Journal of Chromatography A. vol. 411, 1987, pp. 345-354).
Kester et al. (J. Infect. Dis. Feb. 15, 2001;183(4):640-7. Epub Jan. 24, 2001).
Viscomi et al. (Journal of Chromatography A. vol. 482, Issue 1, 1999, pp. 99-106).
Wirtz et al. (Experimental Parasitology, vol. 62, Issue 2, Apr. 1987, pp. 166-172).
Young et al. (Sciencer May 24, 1985;228(4702):958-62).
Zhang et al. (Vaccine. vol. 25, Issue 11, Mar. 1, 2007, pp. 2112-2119).
Int'l Prelim. Report for PCT/US2011/056729 dated May 2, 2013.

* cited by examiner

*Primary Examiner* — Gary Nickol
*Assistant Examiner* — Khatol Shahnan Shah
(74) *Attorney, Agent, or Firm* — McAndrews, Held & Malloy

(57) ABSTRACT

The present invention provides novel nucleotide sequence and other constructs used for expression of novel recombinant *P. falciparum* circumsporozoite proteins in bacterial cells such as *E. coli*. Processes are provided for producing a soluble recombinant *P. falciparum* CSP from *E. coli*. Methods to produce a human-grade, highly immunogenic anti-malaria vaccine based on CSP are shown. The novel recombinant *P. falciparum* circumsporozoite protein by itself or in combination with other malaria antigens or adjuvants can form the basis of an effective malaria vaccine.

21 Claims, 19 Drawing Sheets

FIGURE 1

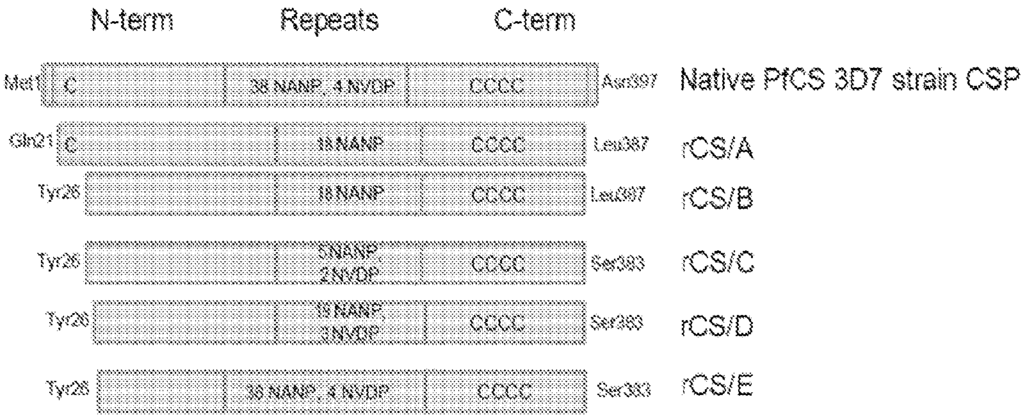

rCS/A sequence: SEQ ID NO: 9
MAHHHHHHPGGSQEYQCYGSSSNTRVLNELNYDNAGTNLYNELEMNYYGKQENWYSLK
KNSRSLGENDDGNNEDNEKLRKPKHKKLKQPADGNPNANPNANPNANPNANPNANPNANP
NANPNANPNANPNANPNANPNANPNANPNANPNANPNANPNANPNANPNKNNQGNGQGHN
MPNDPNRNVDENANANSAVKNNNNEEPSDKHIKEYLNKIQNSLSTEWSPCSVTCGNGIQVRI
KPGSANKPKDELDYANDIEKKICKMEKCSSVFNVVNSSIGL rCS/B sequence: SEQ ID NO: 10
MAHHHHHHPGGSYGSSSNTRVLNELNYDNAGTNLYNELEMNYYGKQENWYSLKKNSRSL
GENDDGNNEDNEKLRKPKHKKLKQPADGNPNANPNANPNANPNANPNANPNANPNANPN
ANPNANPNANPNANPNANPNANPNANPNANPNANPNANPNANPNKNNQGNGQGHNMPNDP
NRNVDENANANSAVKNNNNEEPSDKHIKEYLNKIQNSLSTEWSPCSVTCGNGIQVRIKPGSA
NKPKDELDYANDIEKKICKMEKCSSVFNVVNSSIGL rCS/C serquence: SEQ ID NO: 11
MAHHHHHHPGYGSSSNTRVLNELNYDNAGTNLYNELEMNYYGKQENWYSLKKNSRSLGE
NDDGNNEDNEKLRKPKHKKLKQPADGNPDPNANPNVDPNANPNVDPNANPNANPNANPNK
NNQGNGQGHNMPNDPNRNVDENANANSAGKNNNNEEPSDKHIKEYLNKIQNSLSTEWSPC
SVTCGNGIQVRIKPGSANKPKDELDYANDIEKKICKMEKCSSVFNVVNS rCS/D sequence: SEQ ID NO: 8
MAHHHHHHPGMYGSSSNTRVLNELNYDNAGTNLYNELEMNYYGKQENWYSLKKNSRSL
GENDDGNNEDNEKLRKPKHKKLKQPADGNPDPNANPNVDPNANPNVDPNANPNVDPNANP
NANPNANPNANPNANPNANPNANPNANPNANPNANPNANPNANPNANPNANPNANPNANPN
KNNQGNGQGHNMPNDPNRNVDENANANSAVKNNNNEEPSDKHIKEYLNKIQNSLSTEWSP
CSVTCGNGIQVRIKPGSANKPKDELDYANDIEKKICKMEKCSSVFNVVNSGGRLEHHHHHH

FIGURE 1 (con't)

rCD/E sequence: SEQ ID NO: 12
**<u>MAHHHHHHPGM</u>YGSSSNTRVLNELNYDNAGTNLYNELEMNYYGKQENWYSLKK
NSRSLGENDDGNNEDNEKLRKPKHKKLKQPADGNPDPNANPNVDPNANPNVDPNA
NPNVDPNANPNANPNANPNANPNANPNANPNANPNANPNANPNANPNANPNANPNA
NPNANPNANPNANPNANPNVDPNANPNANPNANPNANPNANPNANPNANPNANPNA
NPNANPNANPNANPNANPNANPNANPNANPNANPNANPNKNNQGNGQGHNMPNDP
NRNVDENANANSAVKNNNNEEPSDKHIKEYLNKIQNSLSTEWSPCSVTCGNGIQVRI
KPGSANKPKDELDYANDIEKKICKMEKCSSVFNVVNS**

*The underlined sequence is from the plasmid (not CSP).

FIGURE 4
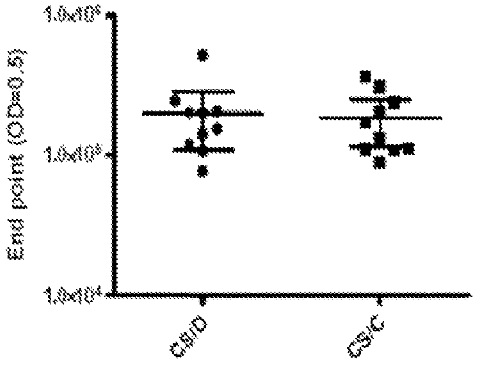
A
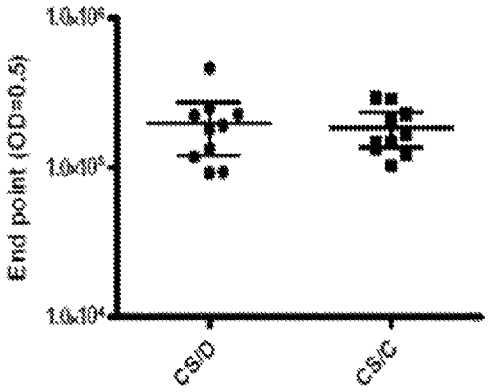
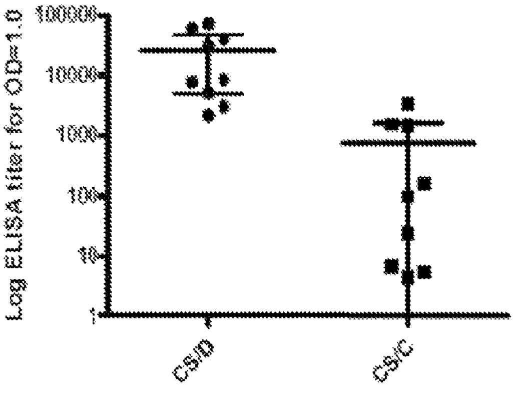
B
C

FIGURE 5

GENE SEQUENCE

SEQ ID NO: 3
Vector encoded N-terminal tag: ATGGCACACCATCATCATCATCATCCCGGGATG

SEQ ID NO: 1- CSP codon optimized gene
TACGGCTCTTCTTCTAACACTCGCGTGCTGAATGAACTGAATTACGATAACGCTGGCACCAA
CCTGTATAATGAACTGGAAATGAACTATTACGGTAAGCAGGAAAACTGGTATAGCCTGAAA
AAGAACAGCCGCAGCCTGGGTGAAAACGACGACGGTAACAACGAGGACAATGAAAAACTG
CGCAAGCCTAAACACAAAAAGCTGAAACAGCCGGCGGACGGTAATCCGGATCCAAACGCAA
ACCCGAATGTGGATCCGAACGCCAATCCGAACGTGGACCCGAACGCGAACCCAAACGTTGA
TCCTAACGCCAACCCGAACGCTAACCCTAACGCCAACCCAAACGCAAACCCTAATGCTAACC
CAAACGCGAACCCGAACGCAAATCCGAACGCGAACCCTAACGCTAACCCTAACGCAAACCC
TAACGCAAACCCAAACGCCAACCCTAACGCGAACCCGAATGCGAATCCGAACGCTAATCCA
AATGCTAACCCGAACAAAAACAACCAGGGCAACGGCCAGGGTCACAATATGCCGAACGATC
CGAATCGCAACGTGGACGAAAATGCTAATGCTAACAGCGCAGTGAAAAACAATAATAACGA
GGAGCCGAGCGATAAGCACATCAAAGAATATCTGAACAAGATCCAGAATAGCCTGTCCACC
GAATGGAGCCCGTGCTCTGTCACGTGCGGTAACGGCATTCAAGTTCGTATCAAAC
CAGGTAGCGCCAACAAGCCGAAAGACGAACTGGACTACGCAAACGACATTGAGAAAAAGA
TCTGTAAAATGGAAAAATGCAGCTCTGTCTTTAACGTCGTTAACTCC

SEQ ID NO: 4: Vector encoded C-terminal tag and stop codon
GGCGGCCGCCTCGAGCACCACCACCACCACCACTGA

SEQ ID NO: 5: CSP codon optimized gene with N- and C- terminal His tag sequences from vector
ATGGCACACCATCATCATCATCATCCCGGGATGTACGGCTCTTCTTCTAACACTCGCGTGCTG
AATGAACTGAATTACGATAACGCTGGCACCAACCTGTATAATGAACTGGAAATGAACTATTA
CGGTAAGCAGGAAAACTGGTATAGCCTGAAAAAGAACAGCCGCAGCCTGGGTGAAAACGA
CGACGGTAACAACGAGGACAATGAAAAACTGCGCAAGCCTAAACACAAAAAGCTGAAACA
GCCGGCGGACGGTAATCCGGATCCAAACGCAAACCCGAATGTGGATCCGAACGCAATCCGA
ACGTGGACCCGAACGCGAACCCAAACGTTGATCCTAACGCCAACCCGAACGCTAACCCTAA
CGCCAACCCAAACGCAAACCCTAATGCTAACCCAAACGCGAACCCGAACGCAAATCCGAAC
GCGAACCCTAACGCTAACCCTAACGCAAACCCTAACGCAAACCCAAACGCCAACCCTAACG
CGAACCCGAATGCGAATCCGAACGCTAATCCAAATGCTAACCCGAACAAAAACAACCAGGG
CAACGGCCAGGGTCACAATATGCCGAACGATCCGAATCGCAACGTGGACGAAAATGCTAAT
GCTAACAGCGCAGTGAAAAACAATAATAACGAGGAGCCGAGCGATAAGCACATCAAAGAA
TATCTGAACAAGATCCAGAATAGCCTGTCCACCGAATGGAGCCCGTGCTCTGTCACGTGCGG
TAACGGCATTCAAGTTCGTATCAAACCAGGTAGCGCCAACAAGCCGAAAGACGAACTGGAC
TACGCAAACGACATTGAGAAAAAGATCTGTAAAATGGAAAAATGCAGCTCTGTCTTTAACG
TCGTTAACTCCGGCGGCCGCCTCGAGCACCACCACCACCACCACTGA

FIGURE 6

PEPTIDE SEQUENCE

SEQ ID NO: 6- Vector encoded N-terminal tag
MAHHHHHHPGM

SEQ ID NO: 2- CSP recombinant protein sequence
YGSSSNTRVLNELNYDNAGTNLYNELEMNYYGKQENWYSLKKNSRSLGENDDGNNED
NEKLRKPKHKKLKQPADGNPDPNANPNVDPNANPNVDPNANPNVDPNANPNANPNAN
PNANPNANPNANPNANPNANPNANPNANPNANPNANPNANPNANPNANPNANPNKNN
QGNGQGHNMPNDPNRNVDENANANSAVKNNNNEEPSDKHIKEYLNKIQNSLSTEWSP
CSVTCGNGIQVRIKPGSANKPKDELDYANDIEKKICKMEKCSSVFNVVNS

SEQ ID NO: 7- Vector encoded C-terminal tag
GGRLEHHHHHH

SEQ ID NO: 8: CSP recombinant protein sequence including N- and C-terminal 6xHIS tags
MAHHHHHHPGMYGSSSNTRVLNELNYDNAGTNLYNELEMNYYGKQENWYSLKKNSR
SLGENDDGNNEDNEKLRKPKHKKLKQPADGNPDPNANPNVDPNANPNVDPNANPNVD
PNANPNANPNANPNANPNANPNANPNANPNANPNANPNANPNANPNANPNANPNANP
NANPNANPNKNNQGNGQGHNMPNDPNRNVDENANANSAVKNNNNEEPSDKHIKEYL
NKIQNSLSTEWSPCSVTCGNGIQVRIKPGSANKPKDELDYANDIEKKICKMEKCSSVFNV
VNSGGRLEHHHHHH FIGURE 8
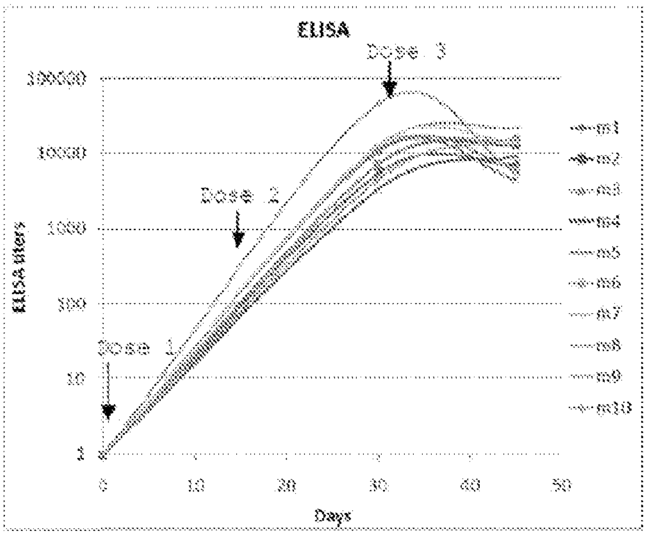
FIG 8A
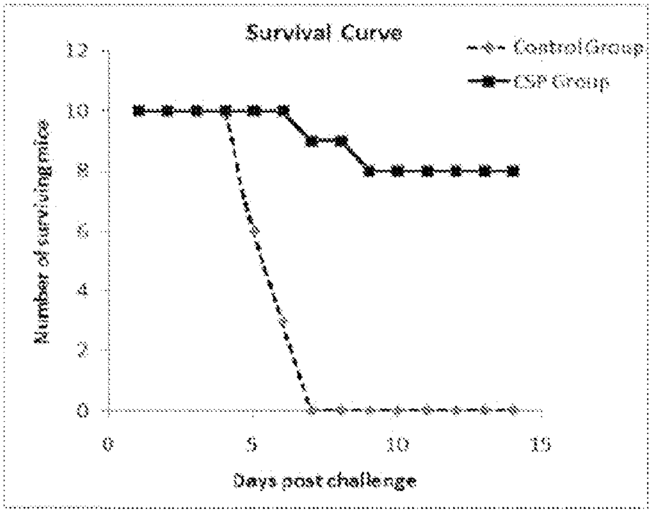
FIG 8B
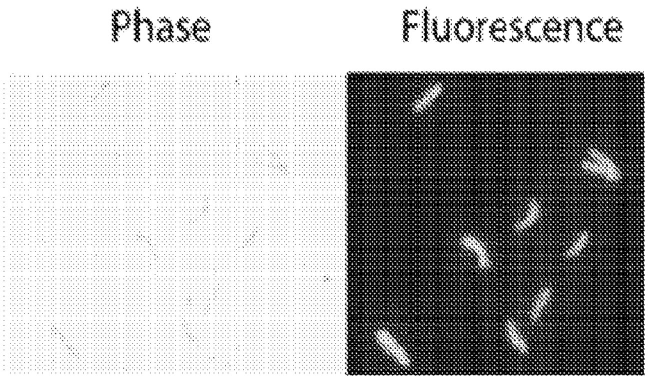
FIG 8C FIGURE 17
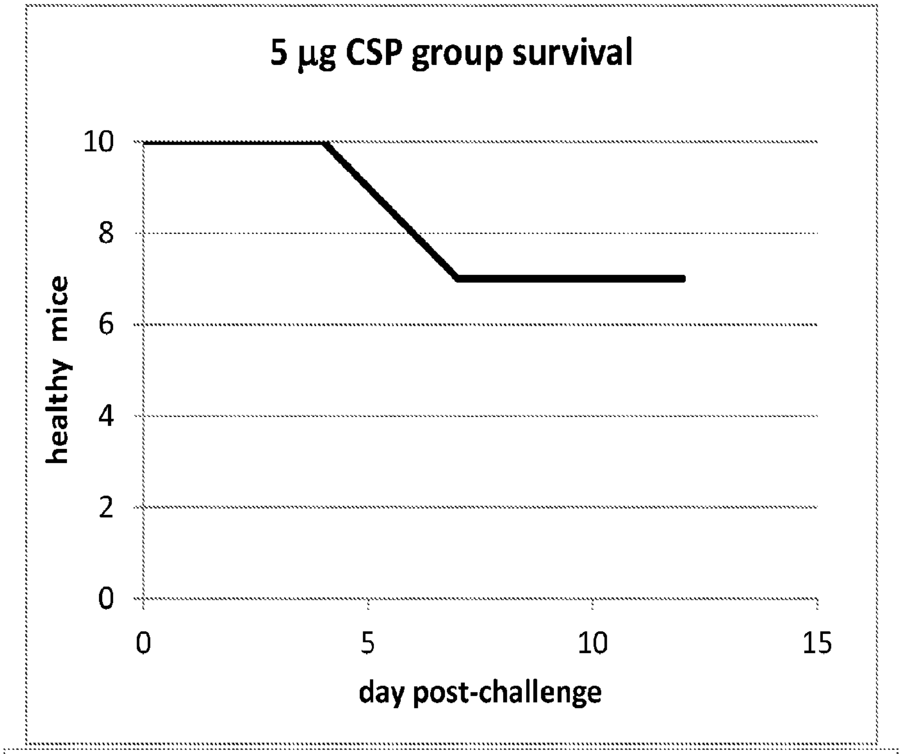
A.
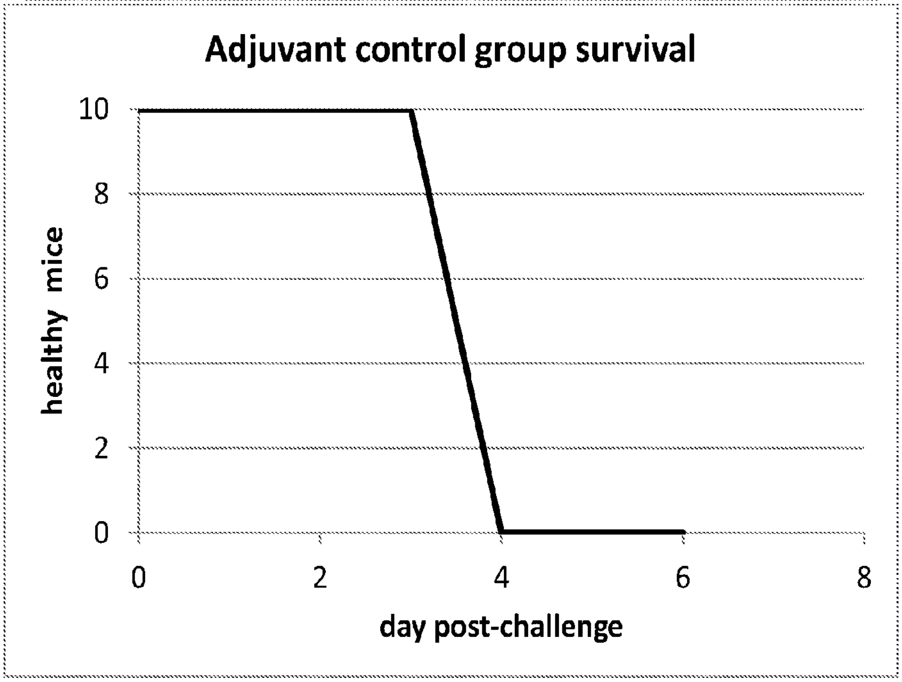
B.

Filled diamond = protected
Open diamond = not protected

SEQUENCE LISTING

```
<160> NUMBER OF SEQ ID NOS: 14

<210> SEQ ID NO 1
<211> LENGTH: 834
<212> TYPE: DNA
<213> ORGANISM: Artificial Sequence
<220> FEATURE:
<223> OTHER INFORMATION: recombinant Plasmodium Falciparum
      circumsporozoite protein nucleic acid sequence

<400> SEQUENCE: 1
```

-continued

```
tacggctctt cttctaacac tcgcgtgctg aatgaactga attacgataa cgctggcacc      60

aacctgtata atgaactgga aatgaactat tacggtaagc aggaaaactg gtatagcctg     120

aaaaagaaca gccgcagcct gggtgaaaac gacgacggta acaacgagga caatgaaaaa     180

ctgcgcaagc ctaaacacaa aaagctgaaa cagccggcgg acggtaatcc ggatccaaac     240

gcaaacccga atgtggatcc gaacgccaat ccgaacgtgg acccgaacgc gaacccaaac     300

gttgatccta acgccaaccc gaacgctaac cctaacgcca acccaaacgc aaaccctaat     360

gctaacccaa acgcgaaccc gaacgcaaat ccgaacgcga accctaacgc taaccctaac     420

gcaaacccta acgcaaaccc aaacgccaac cctaacgcga acccgaatgc gaatccgaac     480

gctaatccaa atgctaaccc gaacaaaaac aaccagggca acggccaggg tcacaatatg     540

ccgaacgatc cgaatcgcaa cgtggacgaa aatgctaatg ctaacagcgc agtgaaaaac     600

aataataacg aggagccgag cgataagcac atcaaagaat atctgaacaa gatccagaat     660

agcctgtcca ccgaatggag cccgtgctct gtcacgtgcg gtaacggcat tcaagttcgt     720

atcaaaccag gtagcgccaa caagccgaaa gacgaactgg actacgcaaa cgacattgag     780

aaaaagatct gtaaaatgga aaaatgcagc tctgtcttta acgtcgttaa ctcc           834
```

```
<210> SEQ ID NO 2
<211> LENGTH: 278
<212> TYPE: PRT
<213> ORGANISM: Artificial Sequence
<220> FEATURE:
<223> OTHER INFORMATION: recombinant Plasmodium Falciparum
      circumsporozoite polypeptide sequence

<400> SEQUENCE: 2

Tyr Gly Ser Ser Ser Asn Thr Arg Val Leu Asn Glu Leu Asn Tyr Asp
1               5                   10                  15

Asn Ala Gly Thr Asn Leu Tyr Asn Glu Leu Glu Met Asn Tyr Tyr Gly
            20                  25                  30

Lys Gln Glu Asn Trp Tyr Ser Leu Lys Lys Asn Ser Arg Ser Leu Gly
        35                  40                  45

Glu Asn Asp Asp Gly Asn Asn Glu Asp Asn Glu Lys Leu Arg Lys Pro
    50                  55                  60

Lys His Lys Lys Leu Lys Gln Pro Ala Asp Gly Asn Pro Asp Pro Asn
65                  70                  75                  80

Ala Asn Pro Asn Val Asp Pro Asn Ala Asn Pro Asn Val Asp Pro Asn
                85                  90                  95

Ala Asn Pro Asn Val Asp Pro Asn Ala Asn Pro Asn Ala Asn Pro Asn
            100                 105                 110

Ala Asn Pro Asn Ala Asn Pro Asn Ala Asn Pro Asn Ala Asn Pro Asn
        115                 120                 125

Ala Asn Pro Asn Ala Asn Pro Asn Ala Asn Pro Asn Ala Asn Pro Asn
    130                 135                 140

Ala Asn Pro Asn Ala Asn Pro Asn Ala Asn Pro Asn Ala Asn Pro Asn
145                 150                 155                 160

Ala Asn Pro Asn Ala Asn Pro Asn Lys Asn Asn Gln Gly Asn Gly Gln
                165                 170                 175

Gly His Asn Met Pro Asn Asp Pro Asn Arg Asn Val Asp Glu Asn Ala
            180                 185                 190

Asn Ala Asn Ser Ala Val Lys Asn Asn Asn Asn Glu Glu Pro Ser Asp
        195                 200                 205
```

-continued

```
Lys His Ile Lys Glu Tyr Leu Asn Lys Ile Gln Asn Ser Leu Ser Thr
    210                 215                 220

Glu Trp Ser Pro Cys Ser Val Thr Cys Gly Asn Gly Ile Gln Val Arg
225                 230                 235                 240

Ile Lys Pro Gly Ser Ala Asn Lys Pro Lys Asp Glu Leu Asp Tyr Ala
                245                 250                 255

Asn Asp Ile Glu Lys Lys Ile Cys Lys Met Glu Lys Cys Ser Ser Val
            260                 265                 270

Phe Asn Val Val Asn Ser
        275


<210> SEQ ID NO 3
<211> LENGTH: 33
<212> TYPE: DNA
<213> ORGANISM: Escherichia coli
<220> FEATURE:
<221> NAME/KEY: misc_feature
<223> OTHER INFORMATION: E. coli derived N terminal 6X-His tag
      nucleotide sequence derived from E. coli vector

<400> SEQUENCE: 3

atggcacacc atcatcatca tcatcccggg atg                                33


<210> SEQ ID NO 4
<211> LENGTH: 36
<212> TYPE: DNA
<213> ORGANISM: Escherichia coli
<220> FEATURE:
<221> NAME/KEY: misc_feature
<223> OTHER INFORMATION: E. Coli derived C-terminal 6XHIS tag nucleotide
      sequence derived from E. coli vector

<400> SEQUENCE: 4

ggcggccgcc tcgagcacca ccaccaccac cactga                             36


<210> SEQ ID NO 5
<211> LENGTH: 902
<212> TYPE: DNA
<213> ORGANISM: Artificial Sequence
<220> FEATURE:
<223> OTHER INFORMATION: rCS/D; recombinant Plasmodium Falciparum
      circumsporozoite protein nucleic acid sequence with 19 NANP
      repeats and 3 NVDP repeats, and including N and C terminal 6X HIS
      tags

<400> SEQUENCE: 5

atggcacacc atcatcatca tcatcccggg atgtacggct cttcttctaa cactcgcgtg     60

ctgaatgaac tgaattacga taacgctggc accaacctgt ataatgaact ggaaatgaac    120

tattacggta agcaggaaaa ctggtatagc ctgaaaaaga acagccgcag cctgggtgaa    180

aacgacgacg gtaacaacga ggacaatgaa aaactgcgca agcctaaaca caaaaagctg    240

aaacagccgg cggacggtaa tccggatcca aacgcaaacc cgaatgtgga tccgaacgca    300

atccgaacgt ggacccgaac gcgaacccaa acgttgatcc taacgccaac ccgaacgcta    360

accctaacgc caacccaaac gcaaacccta atgctaaccc aaacgcgaac ccgaacgcaa    420

atccgaacgc gaaccctaac gctaacccta acgcaaaccc taacgcaaac ccaaacgcca    480

accctaacgc gaacccgaat gcgaatccga acgctaatcc aaatgctaac ccgaacaaaa    540

acaaccaggg caacggccag ggtcacaata tgccgaacga tccgaatcgc aacgtggacg    600

aaaatgctaa tgctaacagc gcagtgaaaa acaataataa cgaggagccg agcgataagc    660

acatcaaaga atatctgaac aagatccaga atagcctgtc caccgaatgg agcccgtgct    720
```

```
ctgtcacgtg cggtaacggc attcaagttc gtatcaaacc aggtagcgcc aacaagccga    780

aagacgaact ggactacgca aacgacattg agaaaaagat ctgtaaaatg gaaaaatgca    840

gctctgtctt taacgtcgtt aactccggcg gccgcctcga gcaccaccac caccaccact    900

ga                                                                   902


<210> SEQ ID NO 6
<211> LENGTH: 11
<212> TYPE: PRT
<213> ORGANISM: Escherichia coli
<220> FEATURE:
<221> NAME/KEY: MISC_FEATURE
<223> OTHER INFORMATION: N-terminal 6X HIS tag polypeptide sequence
      derived from E. coli vector

<400> SEQUENCE: 6

Met Ala His His His His His His Pro Gly Met
1               5                   10


<210> SEQ ID NO 7
<211> LENGTH: 11
<212> TYPE: PRT
<213> ORGANISM: Escherichia coli
<220> FEATURE:
<221> NAME/KEY: MISC_FEATURE
<223> OTHER INFORMATION: C-terminal 6X HIS tag polypeptide sequence
      derived from E. coli vector

<400> SEQUENCE: 7

Gly Gly Arg Leu Glu His His His His His His
1               5                   10


<210> SEQ ID NO 8
<211> LENGTH: 300
<212> TYPE: PRT
<213> ORGANISM: Artificial Sequence
<220> FEATURE:
<223> OTHER INFORMATION: rCS/D; recombinant Plasmodium Falciparum
      circumsporozoite polypeptide sequence including an N- and
      C-terminal E. Coli derived 6X HIS tags and Tyr26 start amino acid
      of CSP

<400> SEQUENCE: 8

Met Ala His His His His His His Pro Gly Met Tyr Gly Ser Ser Ser
1               5                   10                  15

Asn Thr Arg Val Leu Asn Glu Leu Asn Tyr Asp Asn Ala Gly Thr Asn
            20                  25                  30

Leu Tyr Asn Glu Leu Glu Met Asn Tyr Tyr Gly Lys Gln Glu Asn Trp
        35                  40                  45

Tyr Ser Leu Lys Lys Asn Ser Arg Ser Leu Gly Glu Asn Asp Asp Gly
    50                  55                  60

Asn Asn Glu Asp Asn Glu Lys Leu Arg Lys Pro Lys His Lys Lys Leu
65                  70                  75                  80

Lys Gln Pro Ala Asp Gly Asn Pro Asp Pro Asn Ala Asn Pro Asn Val
                85                  90                  95

Asp Pro Asn Ala Asn Pro Asn Val Asp Pro Asn Ala Asn Pro Asn Val
            100                 105                 110

Asp Pro Asn Ala Asn Pro Asn Ala Asn Pro Asn Ala Asn Pro Asn Ala
        115                 120                 125

Asn Pro Asn Ala Asn Pro Asn Ala Asn Pro Asn Ala Asn Pro Asn Ala
    130                 135                 140
```

-continued

```
Asn Pro Asn Ala Asn Pro Asn Ala Asn Pro Asn Ala Asn Pro Asn Ala
145                 150                 155                 160

Asn Pro Asn Ala Asn Pro Asn Ala Asn Pro Asn Ala Asn Pro Asn Ala
                165                 170                 175

Asn Pro Asn Lys Asn Asn Gln Gly Asn Gly Gln Gly His Asn Met Pro
            180                 185                 190

Asn Asp Pro Asn Arg Asn Val Asp Glu Asn Ala Asn Ala Asn Ser Ala
        195                 200                 205

Val Lys Asn Asn Asn Asn Glu Glu Pro Ser Asp Lys His Ile Lys Glu
    210                 215                 220

Tyr Leu Asn Lys Ile Gln Asn Ser Leu Ser Thr Glu Trp Ser Pro Cys
225                 230                 235                 240

Ser Val Thr Cys Gly Asn Gly Ile Gln Val Arg Ile Lys Pro Gly Ser
                245                 250                 255

Ala Asn Lys Pro Lys Asp Glu Leu Asp Tyr Ala Asn Asp Ile Glu Lys
            260                 265                 270

Lys Ile Cys Lys Met Glu Lys Cys Ser Ser Val Phe Asn Val Val Asn
        275                 280                 285

Ser Gly Gly Arg Leu Glu His His His His His His
    290                 295                 300


<210> SEQ ID NO 9
<211> LENGTH: 281
<212> TYPE: PRT
<213> ORGANISM: Artificial Sequence
<220> FEATURE:
<223> OTHER INFORMATION: rCS/A- recombinant Plasmodium Falciparum
      circumsporozoite polypeptide sequence with 18 NANP repeats and
      Gln21 starting amino acid and an N-terminal 6X HIS tag

<400> SEQUENCE: 9

Met Ala His His His His His His Pro Gly Gly Ser Gln Glu Tyr Gln
1               5                   10                  15

Cys Tyr Gly Ser Ser Ser Asn Thr Arg Val Leu Asn Glu Leu Asn Tyr
            20                  25                  30

Asp Asn Ala Gly Thr Asn Leu Tyr Asn Glu Leu Glu Met Asn Tyr Tyr
        35                  40                  45

Gly Lys Gln Glu Asn Trp Tyr Ser Leu Lys Lys Asn Ser Arg Ser Leu
    50                  55                  60

Gly Glu Asn Asp Asp Gly Asn Asn Glu Asp Asn Glu Lys Leu Arg Lys
65                  70                  75                  80

Pro Lys His Lys Lys Leu Lys Gln Pro Ala Asp Gly Asn Pro Asn Ala
                85                  90                  95

Asn Pro Asn Ala Asn Pro Asn Ala Asn Pro Asn Ala Asn Pro Asn Ala
            100                 105                 110

Asn Pro Asn Ala Asn Pro Asn Ala Asn Pro Asn Ala Asn Pro Asn Ala
        115                 120                 125

Asn Pro Asn Ala Asn Pro Asn Ala Asn Pro Asn Ala Asn Pro Asn Ala
    130                 135                 140

Asn Pro Asn Ala Asn Pro Asn Ala Asn Pro Asn Ala Asn Pro Asn Ala
145                 150                 155                 160

Asn Pro Asn Ala Asn Pro Asn Lys Asn Asn Gln Gly Asn Gly Gln Gly
                165                 170                 175

His Asn Met Pro Asn Asp Pro Asn Arg Asn Val Asp Glu Asn Ala Asn
            180                 185                 190

Ala Asn Ser Ala Val Lys Asn Asn Asn Asn Glu Glu Pro Ser Asp Lys
```

```
        195                 200                 205

His Ile Lys Glu Tyr Leu Asn Lys Ile Gln Asn Ser Leu Ser Thr Glu
    210                 215                 220

Trp Ser Pro Cys Ser Val Thr Cys Gly Asn Gly Ile Gln Val Arg Ile
225                 230                 235                 240

Lys Pro Gly Ser Ala Asn Lys Pro Lys Asp Glu Leu Asp Tyr Ala Asn
                245                 250                 255

Asp Ile Glu Lys Lys Ile Cys Lys Met Glu Lys Cys Ser Ser Val Phe
            260                 265                 270

Asn Val Val Asn Ser Ser Ile Gly Leu
        275                 280


<210> SEQ ID NO 10
<211> LENGTH: 276
<212> TYPE: PRT
<213> ORGANISM: Artificial Sequence
<220> FEATURE:
<223> OTHER INFORMATION: rCS/B- recombinant Plasmodium Falciparum
      circumsporozoite polypeptide sequence with 18 NANP repeats and
      Tyr26 start amino acid and an N-terminal 6X HIS tag

<400> SEQUENCE: 10

Met Ala His His His His His His Pro Gly Gly Ser Tyr Gly Ser Ser
1               5                   10                  15

Ser Asn Thr Arg Val Leu Asn Glu Leu Asn Tyr Asp Asn Ala Gly Thr
            20                  25                  30

Asn Leu Tyr Asn Glu Leu Glu Met Asn Tyr Tyr Gly Lys Gln Glu Asn
        35                  40                  45

Trp Tyr Ser Leu Lys Lys Asn Ser Arg Ser Leu Gly Glu Asn Asp Asp
    50                  55                  60

Gly Asn Asn Glu Asp Asn Glu Lys Leu Arg Lys Pro Lys His Lys Lys
65                  70                  75                  80

Leu Lys Gln Pro Ala Asp Gly Asn Pro Asn Ala Asn Pro Asn Ala Asn
                85                  90                  95

Pro Asn Ala Asn Pro Asn Ala Asn Pro Asn Ala Asn Pro Asn Ala Asn
            100                 105                 110

Pro Asn Ala Asn Pro Asn Ala Asn Pro Asn Ala Asn Pro Asn Ala Asn
        115                 120                 125

Pro Asn Ala Asn Pro Asn Ala Asn Pro Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Lys Asn Asn Gln Gly Asn Gly Gln Gly His Asn Met Pro Asn
                165                 170                 175

Asp Pro Asn Arg Asn Val Asp Glu Asn Ala Asn Ala Asn Ser Ala Val
            180                 185                 190

Lys Asn Asn Asn Asn Glu Glu Pro Ser Asp Lys His Ile Lys Glu Tyr
        195                 200                 205

Leu Asn Lys Ile Gln Asn Ser Leu Ser Thr Glu Trp Ser Pro Cys Ser
    210                 215                 220

Val Thr Cys Gly Asn Gly Ile Gln Val Arg Ile Lys Pro Gly Ser Ala
225                 230                 235                 240

Asn Lys Pro Lys Asp Glu Leu Asp Tyr Ala Asn Asp Ile Glu Lys Lys
                245                 250                 255

Ile Cys Lys Met Glu Lys Cys Ser Ser Val Phe Asn Val Val Asn Ser
            260                 265                 270
```

-continued

```
Ser Ile Gly Leu
        275


<210> SEQ ID NO 11
<211> LENGTH: 228
<212> TYPE: PRT
<213> ORGANISM: Artificial Sequence
<220> FEATURE:
<223> OTHER INFORMATION: rCS/C- recombinant Plasmodium Falciparum
      circumsporozoite polypeptide with 5 NANP repeats and 2 NVDP
      repeats and Tyr26 start amino acid and a N-terminal 6X HIS tag
      sequence

<400> SEQUENCE: 11

Met Ala His His His His His His Pro Gly Tyr Gly Ser Ser Ser Asn
1               5                   10                  15

Thr Arg Val Leu Asn Glu Leu Asn Tyr Asp Asn Ala Gly Thr Asn Leu
            20                  25                  30

Tyr Asn Glu Leu Glu Met Asn Tyr Tyr Gly Lys Gln Glu Asn Trp Tyr
        35                  40                  45

Ser Leu Lys Lys Asn Ser Arg Ser Leu Gly Glu Asn Asp Asp Gly Asn
    50                  55                  60

Asn Glu Asp Asn Glu Lys Leu Arg Lys Pro Lys His Lys Lys Leu Lys
65                  70                  75                  80

Gln Pro Ala Asp Gly Asn Pro Asp Pro Asn Ala Asn Pro Asn Val Asp
                85                  90                  95

Pro Asn Ala Asn Pro Asn Val Asp Pro Asn Ala Asn Pro Asn Ala Asn
            100                 105                 110

Pro Asn Ala Asn Pro Asn Lys Asn Asn Gln Gly Asn Gly Gln Gly His
        115                 120                 125

Asn Met Pro Asn Asp Pro Asn Arg Asn Val Asp Glu Asn Ala Asn Ala
    130                 135                 140

Asn Ser Ala Gly Lys Asn Asn Asn Asn Glu Glu Pro Ser Asp Lys His
145                 150                 155                 160

Ile Lys Glu Tyr Leu Asn Lys Ile Gln Asn Ser Leu Ser Thr Glu Trp
                165                 170                 175

Ser Pro Cys Ser Val Thr Cys Gly Asn Gly Ile Gln Val Arg Ile Lys
            180                 185                 190

Pro Gly Ser Ala Asn Lys Pro Lys Asp Glu Leu Asp Tyr Ala Asn Asp
        195                 200                 205

Ile Glu Lys Lys Ile Cys Lys Met Glu Lys Cys Ser Ser Val Phe Asn
    210                 215                 220

Val Val Asn Ser
225


<210> SEQ ID NO 12
<211> LENGTH: 369
<212> TYPE: PRT
<213> ORGANISM: Artificial Sequence
<220> FEATURE:
<223> OTHER INFORMATION: rCS/E- recombinant Plasmodium Falciparum
      circumsporozoite polypeptide with 38 NANP repeats and 4 NVDP
      repeats and Tyr26 start amino acid and a N-terminal 6X HIS tag
      sequence

<400> SEQUENCE: 12

Met Ala His His His His His His Pro Gly Met Tyr Gly Ser Ser Ser
1               5                   10                  15

Asn Thr Arg Val Leu Asn Glu Leu Asn Tyr Asp Asn Ala Gly Thr Asn
```

-continued 20 25 30

Leu Tyr Asn Glu Leu Glu Met Asn Tyr Tyr Gly Lys Gln Glu Asn Trp
35 40 45

Tyr Ser Leu Lys Lys Asn Ser Arg Ser Leu Gly Glu Asn Asp Asp Gly
50 55 60

Asn Asn Glu Asp Asn Glu Lys Leu Arg Lys Pro Lys His Lys Lys Leu
65 70 75 80

Lys Gln Pro Ala Asp Gly Asn Pro Asp Pro Asn Ala Asn Pro Asn Val
85 90 95

Asp Pro Asn Ala Asn Pro Asn Val Asp Pro Asn Ala Asn Pro Asn Val
100 105 110

Asp Pro Asn Ala Asn Pro Asn Ala Asn Pro Asn Ala Asn Pro Asn Ala
115 120 125

Asn Pro Asn Ala Asn Pro Asn Ala Asn Pro Asn Ala Asn Pro Asn Ala
130 135 140

Asn Pro Asn Ala Asn Pro Asn Ala Asn Pro Asn Ala Asn Pro Asn Ala
145 150 155 160

Asn Pro Asn Ala Asn Pro Asn Ala Asn Pro Asn Ala Asn Pro Asn Ala
165 170 175

Asn Pro Asn Ala Asn Pro Asn Val Asp Pro Asn Ala Asn Pro Asn Ala
180 185 190

Asn Pro Asn Ala Asn Pro Asn Ala Asn Pro Asn Ala Asn Pro Asn Ala
195 200 205

Asn Pro Asn Ala Asn Pro Asn Ala Asn Pro Asn Ala Asn Pro Asn Ala
210 215 220

Asn Pro Asn Ala Asn Pro Asn Ala Asn Pro Asn Ala Asn Pro Asn Ala
225 230 235 240

Asn Pro Asn Ala Asn Pro Asn Ala Asn Pro Asn Ala Asn Pro Asn Ala
245 250 255

Asn Pro Asn Lys Asn Asn Gln Gly Asn Gly Gln Gly His Asn Met Pro
260 265 270

Asn Asp Pro Asn Arg Asn Val Asp Glu Asn Ala Asn Ala Asn Ser Ala
275 280 285

Val Lys Asn Asn Asn Asn Glu Glu Pro Ser Asp Lys His Ile Lys Glu
290 295 300

Tyr Leu Asn Lys Ile Gln Asn Ser Leu Ser Thr Glu Trp Ser Pro Cys
305 310 315 320

Ser Val Thr Cys Gly Asn Gly Ile Gln Val Arg Ile Lys Pro Gly Ser
325 330 335

Ala Asn Lys Pro Lys Asp Glu Leu Asp Tyr Ala Asn Asp Ile Glu Lys
340 345 350

Lys Ile Cys Lys Met Glu Lys Cys Ser Ser Val Phe Asn Val Val Asn
355 360 365

Ser

<210> SEQ ID NO 13
<211> LENGTH: 4
<212> TYPE: PRT
<213> ORGANISM: Artificial Sequence
<220> FEATURE:
<223> OTHER INFORMATION: Repeat sequence derived from P. falciparum CSP

<400> SEQUENCE: 13

Asn Ala Asn Pro
1

-continued

```
<210> SEQ ID NO 14
<211> LENGTH: 4
<212> TYPE: PRT
<213> ORGANISM: Artificial Sequence
<220> FEATURE:
<223> OTHER INFORMATION: Repeat sequence derived from P. falciparum CSP

<400> SEQUENCE: 14

Asn Val Asp Pro
1
```

PLASMODIUM FALCIPARUM CIRCUMSPOROZOITE VACCINE GENE OPTIMIZATION FOR SOLUBLE PROTEIN EXPRESSION

CROSS-REFERENCE TO RELATED APPLICATION

This application claims the benefit of priority from U.S. Provisional Patent Application No. 61/394,048 entitled "*Plasmodium Falciparum* Circumsporozoite Vaccine Gene Optimization for Soluble Protein Expression" filed on Oct. 18, 2010, which is incorporated by reference in its entirety.

RIGHTS IN THE INVENTION

The present invention was made with support from the United States Government and, specifically, the Walter Reed Army Institute of Research, and, accordingly, the United States government has certain rights in this invention.

TECHNICAL FIELD

The present technology is directed generally to recombinant *Plasmodium falciparum* circumsporozoite proteins, to methods for production of those proteins, and to vaccines including those proteins, among other aspects.

BACKGROUND

A malaria parasite infected mosquito can inject approximately 100-200 *Plasmodium sporozoites* under the human skin during a blood meal. These sporozoites travel a considerable distance through several layers of tissue to reach the liver. The sporozoite journey from skin to the liver can take several minutes, during which it is exposed to the host immune system. Each successful sporozoite invasion can yield ~30,000 blood stage merozoites, each capable of invading an RBC seconds after its release (Blum-Tirouvanziam, Servis et al. 1995). Hence immune interventions that block sporozoite invasion can be the most effective strategy to induce sterile immunity in humans (Blum-Tirouvanziam, Servis et al. 1995). The most abundant sporozoite surface protein of *P. falciparum* is the 397 amino acid long Circumsporozoite protein (CSP). A comparison of amino acid sequences of CSP across the genus *Plasmodium* revealed a highly conserved gene structure (Doolan, Saul et al. 1992). The central region of the gene consists of a species specific repeat sequence flanked by a N-terminal region that contains a conserved stretch of a five amino acid sequence called "region I" and the C-terminal that contains a conserved cell-adhesive motif similar to one found on thrombospondin.

The functional role of CSP in the life cycle of the parasite is multifaceted. Genetic knockout studies with CSP show its involvement in development of sporozoites from mosquito oocysts (Menard, Sultan et al. 1997). CSP also binds specifically to salivary glands and is involved in the movement of sporozoites from oocysts to the salivary glands (Wang, Fujioka et al. 2005) (Myung, Marshall et al. 2004). Genetic replacement of *P. berghei* CSP with the corresponding CSP from the avian malaria parasite *P. gallinaceum* showed a failure to invade mosquito salivary glands and to infect mice (Tewari R, Rathore D, et al. 2005). Once on the surface of the infective sporozoite stage, the N- and C-terminal regions of CSP have an adhesive function that along with the thrombospondin-related adhesive protein allow the sporozoite binding to heparan sulfate proteoglycans on the liver cell (Frevert 1999). CSP is also known to shield the sporozoite as it traverses through several layers of host tissues including professional phagocytes (Usynin, Klotz et al. 2007) and inhibits host cell protein synthesis. After invasion CSP gets exported into the hepatocyte cytoplasm and the nucleus where it can alter the gene expression profile of the host cell to protect the parasite and promote its growth and maturation (Singh, Buscaglia et al. 2007).

RTS,S is a human malaria vaccine grown in yeast cells and comprises the central repeats and the C-terminal cysteine rich region of *Plasmodium falciparum* CSP, fused to the S antigen of hepatitis B virus. The expressed protein self-assembles into a particle and is formulated with the proprietary adjuvant system ASOX (GlaxoSmithKline, Belgium) that contains immune stimulants MPL and QS21 (Cohen, Nussenzweig et al. 2010). Among the malaria naive individuals, RTS,S vaccination protects approximately 40% of vaccinees against experimental sporozoite challenge (Cohen, Nussenzweig et al. 2010). In a phase 2b trial the efficacy of RTS,S was estimated to be ~35% against first clinical episode and ~49% against severe malaria during an 18-month period among 1- to 4-year-old African children (Alonso, Sacarlal et al. 2004). In another phase II trial among 5-17 month old children, vaccine efficacy of RTS,S against clinical episodes was found to be 53% during an average 8 month period of observation (Bejon, Lusingu et al. 2008).

SUMMARY OF THE INVENTION

The present technology provides novel recombinant *Plasmodium falciparum* circumsporozoite proteins (rCSP), along with nucleotide sequences that express the recombinant *P. falciparum* CSP in bacterial cells, such as *E. coli*, as a soluble protein. The present technology also provides processes of expressing and purifying a soluble recombinant CSP protein without denaturing or refolding the protein. The purified protein produced by the present technology can be greater than 95% pure (that is, the soluble protein present in the composition is greater than 95% rCSP by weight) and contain low levels of endotoxin and low or undetectable levels of host cell proteins when analyzed by current techniques.

As one aspect of the present technology, novel recombinant *Plasmodium falciparum* circumsporozoite proteins are provided. The recombinant *P. falciparum* circumsporozoite proteins are characterized by an N-terminal region that lacks twenty to twenty-five N-terminus amino acid residues of native *P. falciparum* circumsporozoite protein; a reduced number of NANP (SEQ ID NO. 13) repeats compared to native *P. falciparum* circumsporozoite protein; and at least 85% homology to SEQ ID NO:2, alternatively at least 90% homology to SEQ ID NO:2, alternatively at least 95% homology to SEQ ID NO:2. Preferably the recombinant *P. falciparum* circumsporozoite proteins comprise the peptide sequence of SEQ ID NO:2 or SEQ ID NO:8. In some embodiments, the protein lacks $Met_1$ to $Cys_{25}$ of the N-terminal region of native *P. falciparum* circumsporozoite protein. In some embodiments, the protein has 18 or 19 NANP (SEQ ID NO. 13) repeats, preferably 19 NANP (SEQ ID NO: 13) repeats, and/or has 0 to 3 NVDP (SEQ ID NO: 14) repeats, preferably 3 NVDP (SEQ ID NO: 14) repeats. In some embodiments, the recombinant *P. falciparum* CSP has a C-terminal region, preferably one that lacks ten to fourteen C-terminus amino acid residues of native *P. falciparum* circumsporozoite protein, more preferably, the protein ends at $Ser_{383}$.

As another aspect of the present technology, nucleotide sequences are provided which encode a recombinant *P. fal-*

*ciparum* CSP as described in the preceding paragraph or elsewhere in this specification. Suitable nucleotide sequences include nucleotide sequences comprising SEQ ID NO:1 or sequences that are at least 85% homologous to SEQ ID NO:1, alternatively at least 90% homologous to SEQ ID NO:1; alternatively at least 95% homologous to SEQ ID NO:1. The nucleotide sequences can include at least one expression tag, such as the sequence of SEQ ID NO:5.

As another aspect of the present technology, novel expression vectors are provided for *E. coli* comprising a nucleotide sequence which encodes a recombinant *P. falciparum* CSP as described herein. The expression vectors can be stably cloned into a bacterial cell. A suitable bacterial cell can be transformed with such an expression vector. Preferably the bacterial cell is an *E. coli* cell, more preferably the SHUFFLE™ strain of *E. coli*. (New England Biolabs, Inc., Ipswhich, Mass., described in U.S. Pat. No. 6,569,669, incorporated by reference). Surprisingly, the transfected *E. coli* cell expresses a recombinant *P. falciparum* CSP as a soluble protein.

As yet another aspect of the present technology, anti-malaria vaccines suitable for human administration are provided. The vaccines comprise a recombinant *Plasmodium falciparum* CSP as described herein, and one or more adjuvants. Preferred embodiments of the vaccines have an endotoxin level less than about 5 endotoxin units per microgram of protein, and/or less than about 1 ng/ml of bacterial host proteins. In some embodiments, the vaccines have a soluble protein content, and the soluble protein content is greater than 95%, alternatively greater than 99%, pure recombinant *P. falciparum* CSP as measured by gel densitometry.

As another aspect of the present technology, methods of eliciting an immune response against malaria in an animal or human comprise administering a vaccine or rCSP as described herein. Methods of immunizing an animal or human against malaria or a pathogen that causes malaria are also provided. The methods comprise administering to the animal or human a vaccine or rCSP as described herein. In these methods, the vaccine can be administered intramuscularly or by another route.

As still another aspect of the present technology, processes of producing recombinant *P. falciparum* CSP are provided, including processes of producing rCSP in soluble form from *E. coli*. The processes comprise the steps of providing cells, preferably bacterial cells such as *E. coli*, containing a nucleotide sequence that expresses one of the recombinant *P. falciparum* CSPs described herein (such as a transfected *E. coli* that expresses the peptide sequence of SEQ ID NO:2). The cells may be provided in a cell culture. The processes also comprise inducing expression of the recombinant CSP in the cells, and collecting the cells after a period of expression, such as by centrifuging to obtain a pellet containing the cells. The processes also comprise lysing the cells to obtain a cell lysate, collecting supernatant from the cell lysate, and purifying the recombinant *P. falciparum* CSP from the supernatant of the cell lysate without denaturing and refolding the recombinant *P. falciparum* CSP. Preferably, the bacterial cell is cultured in that is media free or substantially free of animal-derived components, such as media containing one or more or all of Phytone, yeast extract, ammonium sulfate, potassium phosphate monobasic, sodium phosphate dibasic, $MgSO_4$, glycerol, dextrose or kanamycin. In some embodiments, the recombinant *P. falciparum* CSP includes one or more expression tags at one or both ends to facilitate the recovery or purification of the protein. The processes can include one or more purification steps, such as purifying the soluble protein over an affinity column and purifying the soluble protein over an anion exchange column, for example, a nickel affinity column and a Q-sepharose anion exchange column. The present technology also includes purified protein made by the processes described herein.

In preferred embodiments of the production processes, purified protein is recovered from a two-step purification procedure over the affinity column and the anion exchange column, and the purification procedure does not include any other chromatographic separation or consists essentially of an affinity column separation on an anion exchange column separation. Alternatively, the production process has no more than two purification steps. The purified protein of the present technology can contain at least about 90% recombinant *P. falciparum* CSP, alternatively at least about 95% or at least about 99%, as measured by gel densitometry. The processes can also include the step of filtering the purified protein. The protein can contain less than 1 ng/ml of *E. coli* host proteins and/or less than about 5 endotoxin units per microgram protein. Preferably the production process meets or exceeds current good manufacturing practices (for example, as described in the US Code of Federal Regulations, Title 21) for vaccine products. The present technology also includes a vaccine comprising a purified protein produced by the foregoing process.

As another aspect, the present technology provides novel CS gene constructs that encode an amino acid sequence having a start site at $Tyr_{26}$, 19 copies of the NANP (SEQ ID NO. 13) amino acid repeat, and 3 copies of the NVDP (SEQ ID NO: 14) repeat. On the C-terminal region, the glycosylphosphatidylinositol (GPI) anchor sequence can be excluded from the CS gene construct and excluded from the rCSP; in other words the CS gene construct does not include a nucleotide sequence that encodes the GPI anchor sequence, and the rCSP does not include the GPI anchor sequence. The novel soluble recombinant proteins of the present technology can comprise a protein sequence with at least 85% homology to SEQ ID NO:2, preferably 90% homology to SEQ ID NO:2, preferably at least 95% homology to SEQ ID NO:2, more preferably about 99% homology to SEQ ID NO:2, most preferably includes SEQ ID NO:2 and in some embodiments include at least one expression tag, preferably at least two expression tags. In some aspects, at least one expression tag is a histidine tag, for example, a 6×HIS tag, preferably two 6×HIS tags, such as in SEQ ID NO:8. Novel nucleotide sequences are provided that encode the soluble CSPs of the present technology, which can be expressed in *E. coli* and have at least 85% homology, preferably at least 90% homology, preferably at least 95% homology, more preferably at least 99% homology to SEQ ID NO:1. In some aspects, the nucleotide sequence encoding the CSP of the present technology comprises nucleotide sequences for at least one expression tag, preferably at least two expression tags (for example, expression tags SEQ ID NO: 3 and SEQ ID NO: 4), and includes SEQ ID NO:5.

In another aspect, the present technology provides vaccines comprising the soluble rCSP disclosed herein and at least one adjuvant. The vaccines can be used to vaccinate a subject (such as a human or animal) and elicit an immune response. In some aspects, the vaccine produces high titer antibodies in the subject.

In some aspects, the novel rCSP induces high titer antibodies when formulated with at least one adjuvant, preferably Montanide ISA 720 adjuvant (Seppic Inc, France). In further aspects, vaccination with the soluble protein of the present technology and at least one adjuvant confers partial or full protection in a vaccinated subject against a malaria challenge, and in some aspects provides sterile protection against malaria challenge.

In another aspect, anti-rCSP antibodies produced after immunization with the soluble protein of the present technology can also recognize native CSP on sporozoites. The present technology includes those anti-rCSP antibodies.

In some aspects, the final recombinant CSP protein of the present technology is of high purity and suitable for human vaccination against malaria. Further, the protein of the present technology can be produced under current good manufacturing practices to produce a vaccine grade protein composition made in animal-free media, a media free of animal-derived components. A human-grade vaccine suitable for administration to human subjects can be produced.

The purified rCSP product of the present technology meets the purity criteria for an injectable for human administration (>95% purity by gel densitometry, low or undetectable levels of host cell proteins, as detected by western blot, and less than 5 endotoxin units/microgram total protein. Further, the rCSP protein product is structurally homogeneous as observed on reduced and non-reduced SDS-page and is stable at 4° C. for at least a week.

In some aspects, the novel rCSP of the present technology is strongly immunogenic and provides protection against challenge of sporozoites.

In some aspects, the present technology provides a method of producing a near full-length soluble CSP (such as the peptide sequence of SEQ ID NO:2) that is stable at high concentrations in aqueous buffer and suitable nucleotide sequences for producing the soluble protein in *E. coli.*

In a further aspect, the present technology provides a PfCSP gene nucleotide sequence that in combination with an *E. coli* host strain produce correctly folded and soluble CSP without requiring a denaturing and refolding step in the production process of the proteins.

In yet a further aspect, the present technology provides a fermentation process that promotes the growth of a CSP-producing bacterial clone in non-animal derived media.

In still another aspect, the present technology provides a two-step purification process which results in a greater than 95% pure product of soluble recombinant CSP with low endotoxin levels (for example, less than 5 endotoxin units per microgram) and low or undetectable levels of host proteins.

In yet another aspect, the present technology provides an *E. coli* host cell that produces a soluble recombinant CSP that can be used for vaccination against malaria. The vaccine containing the CSP can offer improved immunogenicity over yeast derived CSP vaccines which may be post-translationally modified, truncated or glycosylated. Thus, in some embodiments, the present vaccines comprise rCSP that is not glycosylated or post-translationally modified or truncated.

In another aspect, the present technology provides a vaccine that can be economically produced by expression in *E. coli* and a two-step purification system that results in a substantially pure soluble protein.

Other aspects and advantages of the present technology are set forth in part in the description, as follows, and in part, may be obvious from the description, or may be learned from practice of the present technology.

BRIEF DESCRIPTION OF THE FIGURES

FIG. 1 is a cartoon representation of the protein expression constructs CS/A, CS/B, CS/C, CS/D, and CS/E shown in relation to native *P. falciparum* CSP gene 3D7 strain (top). The number of NANP (SEQ ID NO. 13) and NVDP (SEQ ID NO. 14) repeats and relative position of the cysteine residues (C) are also shown (figure not drawn to scale).

FIG. 2A shows purified CS/A (lane 1) and CSB (lane 2) protein as analyzed by SDS-PAGE via coomassie blue staining and western blot analysis using an anti-6×HIS monoclonal antibody after one freeze-thaw cycle. FIG. 2B shows an image of precipitated CS/A protein having a fibrillar structure upon negative staining and electron microscopy imaging. FIG. 2C demonstrates thermal stability of CS/B protein following storage for one week at 37° C. (lane 1), 4° C. (lane 2) and −80° C. (lane 3) as demonstrated by SDS-PAGE and coomassie blue staining.

FIGS. 4A, 4B and 4C illustrate the immunogenicity of rCSP proteins based on the number of NANP (SEQ ID NO. 13) repeats. Groups of mice (9 per group) were immunized with either CS/C (a 5 NANP (SEQ ID NO. 13) repeat rCS protein) or CS/D (a 19 NANP (SEQ ID NO. 13) repeat CS protein). End-point ELISA titers were determined for the mice two weeks after immunization with the second dose of either the CS/C or CS/D protein. Antibody titers were measured using ELISA plates coated with CS/C (FIG. 4A), CS/D (FIG. 4B), or a 6×NANP (SEQ ID NO. 13) repeat peptide (FIG. 4C).

FIG. 5 depicts the nucleotide sequence of the recombinant CSP gene of the present technology with and without two expression 6×HIS tags.

FIG. 6 depicts the translated protein sequence of the soluble CSP and the N and C-terminal tags.

FIG. 7A is a SDS-PAGE analysis of the Ni—NTA Ni affinity elution and Q-sepharose elution stained by coomassie blue. FIG. 7B is the SDS-PAGE analysis of the elution from a Superdex-75 gel filtration column stained with coomassie blue. FIG. 7C is SDS-PAGE analysis of the CS/D purified protein with 2 μg, 1 μg, 0.5 μg, 0.25 μg and 0.1 μg protein loaded per lane (lanes 1-5 respectively) analyzed under non-reducing and reducing conditions and visualized by silver staining (Snap Silver Kit™, Pierce). FIG. 7D is an anti-CSP mAb Western Blot showing 1 μg CS/D protein positively reacting with the anti-*P. falciparum* CSP specific mAb 49-1B2 (left panel, lane 1). Western blot was also performed to determine purity of the protein using an anti-*E. coli* polyclonal antibody (Dako Corp). Lane 1 and 2 contain 1 μg and 2 μg purified CS/D protein respectively and lane 3 contains the lysate of bacteria (right panel).

FIGS. 8A and 8B depict the immunogenicity and protection efficacy of lab-grade CS/D shown in FIG. 7. FIG. 8A shows specific end-point ELISA titers against CS/D protein coated plates. Titers of individual CSP vaccinated mice were plotted against time (end point defined as serum dilution that results in an OD=0.5). Days of vaccination are shown by arrows. FIG. 8B shows the survival curve of the CSP vaccinated and control group of mice following challenge with 5,000 transgenic sporozoites (Tewari, Spaccapelo et al., 2002). FIG. 8C demonstrates the antibody reactivity of CSP vaccinated mouse sera with methanol fixed sporozoites using an immuno-fluorescence assay, showing positive reactivity of anti-CS antibodies in the fluorescence field (right).

FIGS. 17A and 17B depict the survival curves of mice in the cGMP rCSP CS/D vaccine (A) and adjuvant control (B) groups. Mice that did not become infected by blood stage parasites were considered as protected.

DETAILED DESCRIPTION OF THE PREFERRED EMBODIMENTS

Figure 2:
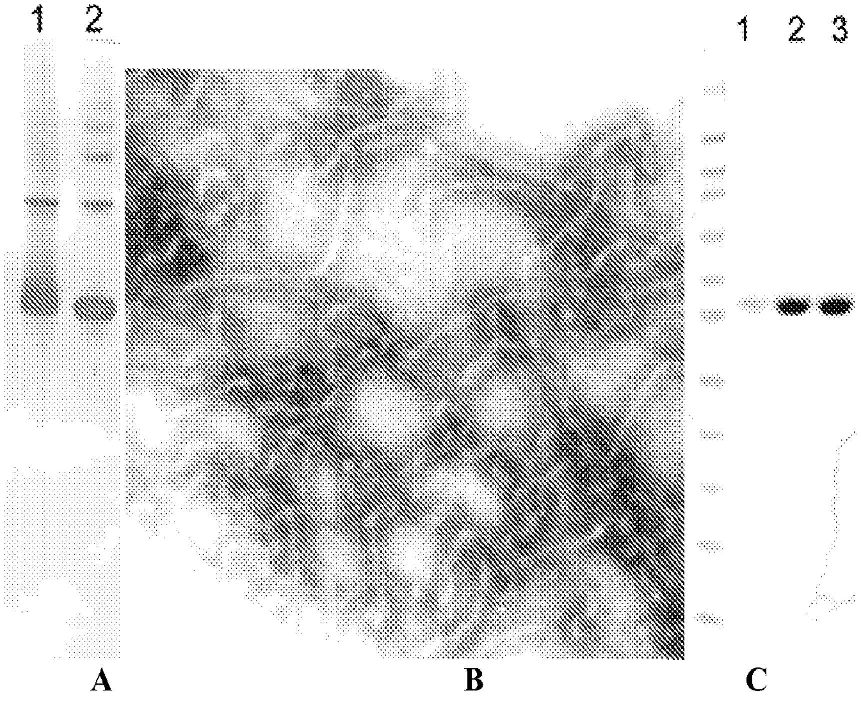
FIGS. 2A, 2B and 2C depict the thermal stability of CS/A and CS/B soluble protein.

In the following detailed description, for purposes of explanation, numerous specific details are set forth in order to provide a thorough understanding of the various embodiments of the present invention. It will be apparent, however, that the various embodiments of the present invention may be practiced without these specific details.

The present technology provides an *E. coli*-produced soluble recombinant CSP and a process to manufacture this protein in a cGMP (current Good Manufacturing Practice, in compliance with CFR Title 21) compliant environment for use as a component of an anti-malarial vaccine. Current GMP for use of products as human injectables is outlined by the Food and Drug Administration in CFR Title 21. For a protein to be used as a human injectable, it has to meet requirements of purity and be grown in conditions that provide a product substantially free of other contaminants.

Expression of the *P. falciparum* CSP gene in *E. coli* has remained a major challenge. The native gene has an AT content of ~65% and it contains several codons for which the cognate tRNA's in *E. coli* are in low abundance (including 6×GGA, 5×AUA, 1×CUA, 3×AGA and 2×AGG codons). The high AT content of PfCSP and the presence of rare codons has made it extremely difficult to express PfCSP in *E. coli*. The complex primary and tertiary structure of CSP pose further problems with prokaryotic expression. This includes two disulphide bonds in the C-terminal region and a highly repetitive NANP (SEQ ID NO. 13) sequence in the middle. Proteins expressed in conventional *E. coli* strains do not form correct disulphide bonds due to the reducing cytosolic environment. The 38 NANP (SEQ ID NO. 13) repeats of PfCSP cause extensive genetic rearrangement during the gene cloning and plasmid maintenance. It is not surprising therefore that expression of a soluble PfCSP in *E. coli* has apparently not been accomplished previously and thus only insoluble protein expression of *P. falciparum* CSP has been reported, that requires extensive in vitro refolding (Kolodny, Kitov et al. 2001, Plassmeyer, Reiter et al. 2009). Another problem with expressing a near full-length CSP is that the N-terminal processing site of native PfCSP is not known, which makes it difficult to determine a suitable start site for the full-length PfCSP based construct for protein expression.

In the literature there are 3 reports of attempted *E. coli* expression of full-length *Plasmodium falciparum* circumsporozoite protein (CSP). The first report showed that full-length CSP gene cannot be expressed in *E. coli* (Young, Hockmeyer et al. 1985). Two subsequent reports showed expression of an insoluble protein product that required extensive refolding to gain solubility (Kolodny, Kitov et al. 2001; Plassmeyer, Reiter et al. 2009). The present technology provides a novel PfCSP gene sequence that yields a highly immunogenic and near full-length soluble recombinant *P. falciparum* circumsporozoite protein (rPfCSP) expressed in *E. coli*. The final rCSP protein is of high purity and suitable for human vaccination against malaria.

In some embodiments, the present technology provides an expression construct for the production of soluble recombinant *P. falciparum* circumsporozoite protein which comprises the peptide sequence SEQ ID NO:2, or a peptide sequence with at least 90% homology to SEQ ID NO:2, more preferably at least 95% homology, more preferably at least 99% homology.

Purification of the expressed protein can be achieved by any suitable means, such as by affinity chromatography using expression tags on the recombinant *P. falciparum* CSP or using antibodies that recognize the appropriate regions of the rCSP. For example, purification by affinity chromatography can be facilitated by including at least one expression tag, preferably at least one polyhistidine tag, e.g. 6×HIS tag, in the recombinant *P. falciparum* CSP. In some preferred embodiments, the recombinant *P. falciparum* CSP includes two expression tags, for example, two polyhistidine tags on one or both of the C-terminus and/or N-terminus of SEQ ID. NO:2. Preferred embodiments of the present technology include the peptide sequence of SEQ ID NO:8, or a peptide sequence that includes the polyhistidine tags and is at least 85% similar to SEQ ID NO: 8, preferably at least about 90% similar to SEQ ID NO: 8, more preferably about 95% or more similar to SEQ ID NO: 8, where SEQ ID NO: 8 is peptide sequence of SEQ ID NO:2 further containing two 6×HIS tag amino acid sequences, one tag on each of the N and C terminus (SEQ ID NO:6 and 7, respectively). The present technology envisions that other expression tags or HIS tag sequences may be used in accordance with the present technology in combination with peptide sequence of SEQ ID NO:2 to produce similar or equivalent results as demonstrated with the soluble protein described herein. The expression tags may be added either at the N-terminus or C-terminus or both. Suitable expression tags include, but are not limited to, myc tag, flag tag, and the like. The total number of histidine residues may vary in the tag. The tag may also be preceded or followed by a suitable amino acid sequence that facilitates a removal of the polyhistidine-tag using endopeptidases. Suitable peptide sequences for N terminal 6×HIS tag include, but are not limited to, SEQ ID NO:6 and suitable peptide sequences for a C-terminal 6×HIS tag include, but are not limited to, SEQ ID NO:7.

In some embodiments, the present technology provides novel nucleotide sequence that encodes the soluble CSP of the present technology which can be expressed in *E. coli* and has at least 85% homology, alternatively at least 90% homology, preferably 95% homology, more preferably 99% homology to SEQ ID NO:1.

In some embodiments, the nucleotide sequence encoding the CSP of the present technology further includes at least one nucleotide sequence, preferably two nucleotide sequences encoding at least one expression tag sequence, preferably at least two expression tag sequences, suitably one or more polyhistidine tag sequences. Suitable polyhistidine sequences include, but are not limited to, 6×HIS, including SEQ ID NO:3 and SEQ ID NO:4. Other suitable expression tag or 6×HIS tag sequences known in the art may be used and are contemplated to be used to express and purify a protein with similar or equivalent characteristics as described in the present technology. The expression tag sequence may be added to the N terminus, C terminus or both of the rCSP gene sequence. A preferred nucleotide sequence of the present technology includes a sequence with at least about 85% homology to SEQ ID NO:5, preferably at least about 90% homology, more preferably at least about 95% homology to SEQ ID NO:5 and includes SEQ ID NO:5, which is the combination of SEQ ID NO:1 with a N-terminal HIS tag (SEQ ID NO:3) and C-terminal HIS tag (SEQ ID NO:4). A suitable nucleotide sequence of the present technology includes SEQ ID NO:1 or a nucleotide sequence that is at least 85% similar to SEQ ID NO: 1, preferably about 90% similar to SEQ ID NO:1, more preferably at least about 95% similar to SEQ ID NO: 1 and includes at least one expression tag sequence, preferably at least two expression tag sequences, most preferably HIS tag sequences.

In some embodiments, the nucleotide sequence of the present technology may be cloned into a suitable expression vector for expression in *E. coli*. Preferably, a nucleotide sequence of the present technology, or for use in the present technology in a vector, is operably linked to a control sequence which is capable of providing for the expression of the coding sequence by the host cell, in other words, the vector is an expression vector. The term “operably linked” refers to a juxtaposition wherein the components described are in a relationship permitting them to function in their intended manner. A regulatory sequence, such as a promoter, “operably linked” to a coding sequence is positioned in such a way that expression of the coding sequence is achieved under conditions compatible with the regulatory sequence.

Suitable expression vectors are known in the art and include, but are not limited to, plasmids, for example, pET plasmid (Novagen, Merck, Whitehouse Station, Mass.) or the pQE plasmids (Qiagen, Valencia, Calif.). The vectors may contain one or more selectable marker genes, for example an ampicillin resistance gene or kanamycin resistance gene in the case of a bacterial plasmid. Promoters and other expression regulation signals may be selected to be compatible with the host *E. coli* cell for which expression is designed to be used. All these promoters are well described and readily available in the art.

In further embodiments, the present technology provides a bacterial cell, such as an *E. coli* cell, transformed with one of nucleotide sequences described above, preferably a nucleotide sequence comprising SEQ ID NO:1, more preferably comprising SEQ ID NO:5. Preferably the bacteria is *E. coli*, and in the preferred embodiments, the *E. coli* strain is the SHUFFLE™ strain.

In another embodiment of the present technology provides a human-grade anti-malaria vaccine. The anti-malaria vaccine comprises a soluble recombinant *P. falciparum* circumsporozoite protein of the present technology. Preferably the vaccine comprises at least one adjuvant and the soluble recombinant protein contains SEQ ID NO:2 and at least one tag sequence, more preferably two expression tags, for example two 6×HIS tags (e.g. SEQ ID NO:8). A human dose of the soluble rCSP can be between about 1 to about 100 micrograms, and the concentration of adjuvant can be determined by one skilled in the art. The rCSP is “soluble” in that it is expressed from a cell, preferably a bacterial cell, without the need for denaturing and refolding. It may or may not be soluble in the vaccine; that is, the vaccine may be a solution, a particle, or a suspension of the rCSP.

The vaccine or purified protein of the present technology comprise low levels of endotoxin, preferably less than about 5 endotoxin units (EU) per microgram protein as measured by chromogenic *Limulus* amebocyte lysate (LAL) endpoint assay (Associates of Cape Cod, Falmouth, Mass.). See e.g., Bacterial Endotoxins Test, United States Pharmacopeia (current revision), United States Pharmacopeial Convention, Rockville, Md. In some embodiments, the vaccine or protein composition of the present technology comprises less than about 2 EU/μg protein, alternatively less than about 1 EU/μg protein, alternatively less than about 0.5 EU/μg protein. In some embodiments, undetectable levels of endotoxin are found in the vaccine or purified protein, for example, less than about 0.1 EU/μg protein by LAL assay. Other suitable assays are known in the art and include, for example, the Gel-clot assay, described in the examples below.

Vaccines of the present technology typically include at least one adjuvant. Suitable adjuvants include, but are not limited to, aluminum salts such as aluminum hydroxide or aluminum phosphate, salts of calcium, iron or zinc, insoluble suspensions of acylated tyrosine, or acylated sugars. Other suitable adjuvants cationically or anionically derivatized saccharides, polyphosphazenes, biodegradable microspheres, nanoparticles, liposome based formulations, monophosphoryl lipid A (MPL), lipid A derivatives (for example, of reduced toxicity), 3-O-deacylated MPL, quil A, Saponin, QS21, Freund’s Incomplete Adjuvant (Difco Laboratories, Detroit, Mich.), Merck Adjuvant 65 (Merck and Company, Inc., Rahway, N.J.), emulsion or a water-in-oil emulsion, ASO (SmithKline Beecham, Philadelphia, Pa.), AS)1 (GlaxoSmithKline), CpG oligonucleotides, bioadhesives and mucoadhesives, polyoxyethylene ether formulations, polyoxyethylene ester formulations, muramyl peptides or imidazoquinolone compounds (e.g. imiquamod and its homologues), or Montanide ISA 720. Human immunomodulators suitable for use as adjuvants in the invention include cytokines such as interleukins (e.g. IL-1, IL-2, IL-4, IL-5, IL-6, IL-7, IL-12, etc.), macrophage colony stimulating factor (M-CSF), tumor necrosis factor (TNF), granulocyte and macrophage colony stimulating factor (GM-CSF). The adjuvant may be provided in the form of microparticles or liposomes containing one or more of the adjuvants disclosed herein or other adjuvants, either inside the particle or on the surface. Alternatively, some adjuvants can be provided in the form of an oil and water emulsion, such as an oil-in-water emulsion or a water-in-oil emulsion. In a preferred embodiment, the adjuvant of the present technology is Montanide ISA 720. In some embodiments, the adjuvant can be selected to induce a specific type of immune response, such as a B-cell response or a T-cell response. In one embodiment of the present technology, the vaccine induces an immune response. Suitable adjuvants which promote an appropriate immune response include, but are not limited to, derivatives of lipid A (preferably of reduced toxicity), Monophosphoryl lipid A (MPL) or a derivative thereof, particularly 3-de-O-acylated monophosphoryl lipid A (3D-MPL), and a combination of monophosphoryl lipid A, optionally 3-de-O-acylated monophosphoryl lipid A together with an aluminum salt.

In some embodiments, the vaccines of the present technology, in addition to the rCS protein and at least one adjuvant, comprise one or more pharmaceutically acceptable carriers or excipients. Excipients include any component that does not itself induce the production of antibodies and is not harmful to the subject receiving the composition. Suitable excipients are typically large, slowly metabolized macromolecules such as proteins, saccharides, polylactic acids, polyglycolic acids, polymeric amino acids, amino acid copolymers, sucrose, trehalose, lactose and lipid aggregates (such as oil droplets or liposomes). Suitable pharmaceutical carriers are well known to those of ordinary skill in the art, including, but not limited to, diluents, such as water, saline, glycerol, and others. Suitably, sterile pyrogen-free, phosphate buffered physiologic saline is a pharmaceutical carrier. Additionally, additives, such as wetting or emulsifying agents, pH buffering substances, and the like, may be present. Vaccines of the present technology are formulated into suitable dosage for the subject to which it is to be administered. The dosage administered may vary with the condition, sex, weight and age of the individual; the route of administration; and the adjuvant used. The vaccine may be used in dosage forms such as suspensions or liquid solutions. The vaccine may be formulated with an pharmaceutically acceptable carrier as described above. Suitable dosages include, but are not limited to, about 1 to about 100 micrograms, alternatively about 5 to about 50 micrograms, of a recombinant CSP described herein.

The present technology provides a method for raising an immune response in a subject, comprising the step of administering an effective amount of a vaccine of the present technology. The vaccines can be administered prophylactically (i.e. to prevent infection) or to provide protective and preferably involves induction of antibodies and/or T cell immunity against CSP. The method may raise a primary immune response, a secondary immune response, a booster response or a combination of immune responses.

Subjects may receive one or several booster (subsequent) immunizations adequately spaced. Dosing treatment can be a single dose schedule or a multiple dose schedule. Multiple doses may be used in a primary immunization schedule and/or in a booster immunization schedule. Suitable timing between the administration of priming doses (e.g. between 4-16 weeks) and between the administration of priming and boosting doses can be determined.

Vaccines of the present technology may be in an aqueous form, for example, but not limited to, solutions, particles or suspensions. The vaccine can be an oil and water emulsion, such as an oil-in-water emulsion or a water-in-oil emulsion. Liquid formulations allow the compositions to be prepackaged and administered direct from their packaged form without the need for reconstitution. Compositions may be presented in vials, or they may be presented in ready filled syringes. A syringe can include a single dose of the composition, whereas a vial may include a single dose or multiple doses (e.g., 2, 3, 4, 5, 10, or more doses). Preferably, the dose is for human administration, suitably for an adult, adolescent, toddler, infant or less than one year old human and may be administered by injection.

The vaccines or compositions of the present technology can be administered by a variety of routes, including, but not limited to, orally, parenterally, subcutaneously, mucosally, intravenously or intramuscularly.

In some embodiments, the vaccine of the present technology comprises recombinant CSP protein and has low or undetectable levels of host cell proteins, preferably less than about 1 ng/ml of host cell proteins. In some embodiments, the amount of host cell proteins would be an undetectable amount, as measured by SDS-PAGE or host cell protein (HSP) ELISA or western blots using antibodies against host cell proteins.

In some embodiments, the soluble protein of the present technology is greater than 95% pure recombinant *P. falciparum* CSP as measured by gel densitometry, preferably at least about 98% pure, more preferably at least about 99% pure recombinant *P. falciparum* CSP as measured by gel densitometry and as evidenced by a single peak by reversed-phase HPLC.

In some embodiments, a combination vaccine comprising the recombinant *P. falciparum* CSP of the present technology and at least one adjuvant is combined with at least one additional malaria antigen. Other suitable malaria antigens are known, including without limitation, for example, blood stage antigens, liver stage antigens, sexual stage antigens, antigens expressed on RBC surface, sporozoite stage antigens and secreted malaria antigens including MSP1, MSP2, MSP3, AMA1, LSA1, Pfs antigens, RON2, and others.

The present technology also provides methods of eliciting an immune response against malaria or malaria antigens in a subject, preferably an animal. The method includes administering to the subject a vaccine comprising the rCSP of the present technology. An immune response includes, but is not limited to, antibody production, killer T-cell responses, and helper T-cell ($T_H$) responses.

In other embodiments, the present technology provides a method of immunizing an animal or human against malaria by administering to the animal the vaccine of the present technology. In some embodiments, immunizing the animal against malaria provides partial or full protective immunity against malaria parasite infection. Preferably the subject is an animal, preferably a primate, more preferably a human.

In other embodiments, the present technology provides a method of producing a recombinant protein of *P. falciparum* circumsporozoite of the present technology in *E. coli*. The recombinant CSP is found produced intracellularly within the E. and can be purified from supernatant of lysed *E. coli* cells expressing the construct. The method includes culturing *E. coli* containing the nucleotide construct comprising the nucleotide sequence of the present technology in non-animal media, pelleting the *E. coli* cells from the *E. coli* culture (by centrifugation), lysing the *E. coli* cells, collecting the supernatant from the *E. coli* lysate, and purifying the soluble protein from the supernatant of the *E. coli* lysate without denaturing and refolding the protein.

In some embodiments, the *E. coli* culture is grown using a fermentation process. The *E. coli* culture can be induced to express the protein using IPTG, preferably at about 0.1 to about 5 mM.

In some embodiments, the purified protein or the vaccine has a host DNA content that is less than or equal to 2 pg per 20 micrograms of purified protein. In some embodiments, the purified protein or the vaccine has a Sarcosyl content below 0.0001%. In some embodiments, the purified protein or the vaccine has a nickel content that is less than or equal to 0.75 micrograms per gram of purified protein or vaccine. In some embodiments, the purified protein or the vaccine has an imidazole content less than 50 nanomoles/mL. In some embodiments, the purified protein or the vaccine has an IPTG content less than or equal to 0.05 micrograms/mL.

In some embodiments, the soluble protein is purified by a two-step process including affinity column and anion exchange column. The soluble protein is purified by flowing the soluble protein over an affinity column, for example a Ni-affinity column and then eluting the bound protein from the column and then flowing the first elutant of soluble protein over a Q-sepharose anion exchange column. Suitable affinity columns include, but not limited to, Ni—NTA affinity columns, cation exchange, anion exchange, tag affinity columns, and gel-filtration columns. Suitable buffers for washing and elution over the affinity and sepharose columns are known to one skilled in the art, and include the buffers as described in the examples below. The protein eluted after the two step purification is at least 95% pure, more preferably at least about 98% pure, more preferably greater than about 98% pure as determined by gel densitometry. The eluted purified protein also has less than 5 EU/ml of endotoxin, preferably less than about 1 EU/ml as measured by the LAL assay and less than 1 ng/ml of host cell proteins as detected by HCP (host cell protein) ELISA.

In some embodiments, the purification includes an additional step of gel filtration. Suitable methods of gel filtration, include, but are not limited to, Superdex™-75 column.

Purified protein may be filtered to provide a sterile product, for example filtered through a cellulose or PVDF based filter, for example, an about 0.2 to about 0.45 micron cellulose filter, preferably a 0.22 micron cellulose filter.

The purified protein of the present technology is stable in aqueous solutions and can be stored for at least a week at 4° C. The purified protein can also be concentrated to at least 0.5 mg/ml, alternatively about between about 1 to about 2 mg/ml.

Example 1

In this Example, the development and expression of a soluble recombinant PfCSP is described. A suitable start site for the recombinant PfCSP was determined as follows. The *P. falciparum* CSP gene contains a signal sequence, followed by the N-terminal region, a region containing 38 NANP (SEQ ID NO. 13) repeats and 4 NVDP (SEQ ID NO. 14) repeats, a C-terminal cysteine-rich region and a glycophosphotidyl inositol (GPI) anchor sequence. On sporozoites, the native CSP is proteolytically processed within the N-terminal region, however the exact N-terminal processing site is unknown. Not to be bound by any theory, but antibodies to a rCSP that includes the processing site may help block the processing step that may play a role in the invasion step required from entry and propagation. Hence, it was hypothesized that a portion of the N terminal region of CSP should be retained in the PfCSP construct of the present technology.

In the absence of the processing site data, two different constructs (namely, CS/A, see SEQ ID NO: 9, FIG. 1 and CS/B, see SEQ ID NO: 10, FIG. 1) were tested for expression in *E. coli*. *P. falciparum* 3D7 strain CSP gene (accession number XP001351122) was used as a template for these sequences. It encodes native PfCSP. The CS/A construct initiated at CSP specific residue $Gln_{21}$ contains 18 of the NANP (SEQ ID NO. 13) repeats and ends at amino acid $Leu_{387}$ (lacking the C-terminal GPI anchor sequence). CS/B only differed from CS/A at the starting residue which was $Tyr_{26}$. CS/A and CS/B were both cloned into pET plasmid, expressed in bacteria, and purified on a Nickel affinity column. Both constructs included His tags on the N-terminus. The purified proteins were tested for stability by freezing and thawing the protein. After a single freeze-thaw cycle the CS/A protein, which included the residue $Cys_{25}$ of native CSP, formed a high molecular weight aggregate that was visualized as a smear on the anti-6His mAb western blot (FIG. 2A, lane 1). CS/A protein solution also showed a visible precipitate that had a fibrillar structure when observed under an electron microscope (FIG. 2B). A majority of the CS/B existed as a monomer after the freeze-thaw (FIG. 2A, lane 2) and only showed the discrete high molecular weight bands corresponding to dimer, trimer and multimers. CS/B was further analyzed for thermal stability over 7 days at 37° C., 4° C. and −80° C. Samples were analyzed using SDS Page and coomassie blue staining. CS/B was found to be stable in solution at 4° C. for at least a week (FIG. 2C, lane 2), while breakdown was observed at 37° C. (FIG. 2C, lane 1). The CS/A protein could only be concentrated to 0.5 mg/ml using ultra-filtration, while the CS/B protein could be concentrated to >1 mg/ml without precipitation. Thus residue $Cys_{25}$ is preferably excluded from the recombinant PfCSP and $Tyr_{26}$ is preferred as the starting amino acid residue of the recombinant PfCSP.

Example 2

Figure 3:
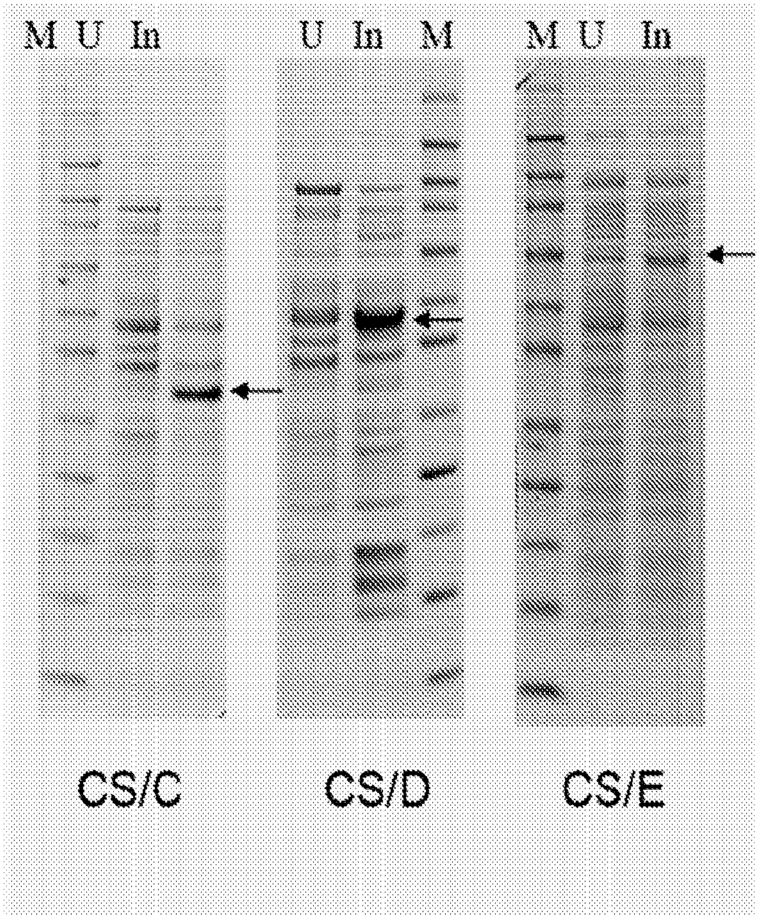
FIG. 3 illustrates the comparative expression levels of CS/C, CS/D, and CS/E in *E. coli*. Uninduced (U) and IPTG induced (In) whole *E. coli* cell pellets were analyzed by SDS-PAGE and stained by coomassie blue. CS/C (5 NANP (SEQ ID NO. 13) repeat containing), CS/D (19 NANP (SEQ ID NO. 13) repeat containing) and CS/E (38 NANP (SEQ ID NO. 13) repeat containing) proteins are shown by the arrows.

The number of NANP (SEQ ID NO. 13) repeats in the recombinant PfCSP was determined as follows. The native *P. falciparum* CSP contains 38 NANP (SEQ ID NO. 13) and 4 NVDP (SEQ ID NO. 14) repeats. The presence of a large number of repeating amino acid units makes it difficult to express CSP in heterologous expression systems. A comparison of the effect of NANP (SEQ ID NO. 13) repeat length on the immunogenicity and expression levels of CSP in *E. coli* was performed. Two different CSP constructs (namely, CS/C, see SEQ ID NO: 11, FIG. 1 and CS/D, see SEQ ID NO: 8, FIG. 1) were transformed and expressed in *E. coli*. Construct CS/C and CS/D had identical N-termini starting at amino acid $Tyr_{26}$ and ending at $Ser_{383}$, the only difference between the two constructs was the number of repeats. CS/C contained 5 NANP (SEQ ID NO. 13) and 2 NVDP (SEQ ID NO. 14) repeats, while CS/D contained 19 NANP (SEQ ID NO. 13) and 3 NVDP (SEQ ID NO. 14) repeats. The proteins were expressed in small scale cultures and the level of expression was compared by running the whole cell lysate of un-induced and IPTG induced bacterial pellets on an SDS PAGE. The recombinant protein were visualized using coomassie blue staining. (FIG. 3). The expression level of the CS/C was found to be the higher than CS/D (FIG. 3) by densitometric analysis with background protein intensity used to normalize the protein load.

The CS/D and CS/C proteins were purified by two steps of column chromatography, and the purified proteins were then used to vaccinate a group of mice using Montanide ISA 720 adjuvant. Two separate doses containing 2.5 micrograms of purified CS/C or CS/D were administered, intra-peritoneally into two groups of 9 mice, 2 weeks apart. Two weeks after the second dose, the sera in mice were collected and were tested for anti-CSP antibodies. Both groups of vaccinated mice (the CS/C group and CS/D group) were found to have similarly high titers of anti-CSP antibodies when tested against whole proteins coated on the plate (FIGS. 4A and 4B). However, the CS/D group titers were significantly higher than the CS/C titers when tested against a repeat peptide '$(NANP)_6$' ((SEQ ID NO. 13) coated on plates (p=0.0002, FIG. 4C), indicating that increasing the number of repeats present in the vaccine protein increases repeat-specific antibody production. Thus, the protein comprising more repeats provides a more potent repeat specific antibody immune response which may be more desirable for an effective CSP based malaria vaccine. A construct that contained all 38 NANP (SEQ ID NO. 13) repeats, CS/E, was also expressed. The expression level of CS/E was however 5 fold lower than CS/D (FIG. 3) as demonstrated by SDS-PAGE coomassie blue staining and densitometric analysis. Thus, CS/D offered a desired balance between bacterial yield and repeat specific immunogenicity.

Example 3

In this example, the amino acid sequence of the native *P. falciparum* 3D7 strain CS protein, derived from the NCBI Genbank (accession number XM_001351086.1) was used to designed a nucleotide sequence that more closely match the codon usage pattern of highly expressed *E. coli* genes without changing the amino acid sequence (for example, the codon-usage tables found at http://www.biology.wustl.edu/gcg/doc-data/ecohigh.cod and www.kazusa.or.jp/codon/ may be used). The resultant gene is shown in SEQ ID NO: 1, FIG. 5. However, similar publically available algorithms may also be used. Codons (AGG, AGA, CGA, CUA, AUA, CCC, ACA, CCU, UCA, GGA, AGU, UCG, GGG) used at a frequency of <1% in *E. coli* were not used in the desired sequence. One-hundred eighty (180) of the 278 rCSP codons were changed, the high AT content of the rPfCSP gene was reduced from 65% to a more balanced 50% following the design effort (FIGS. 5 and 6). The novel synthetic gene was synthesized and cloned into a modified pET based plasmid (Darko, Angov et al. 2005) using the XmaI-NotI restriction sites. Two HIS tags, one on the N-terminus, and one on the C-terminus were added to the PfCSP construct to aid in purification. The CS/D gene was cloned into the pET plasmid in-frame with two vector encoded hexa-histidine tags, one at either end (HIS nucleotide SEQ ID NO:3 and SEQ ID NO:4 in combination with SEQ ID NO:1; see also SEQ ID NO:5, FIG. 5; peptide sequence SEQ ID NO:2 in combination with two HIS tag protein sequences SEQ ID NO:6 and 7, see SEQ ID NO:8).

The expression plasmid was transformed into Top 10 *E. coli* cells (Invitrogen, Carlsbad, Calif.) and sequenced on both strands. The plasmid was then transformed into a series of *E. coli* strains including TUNER™ (Novagen, EMD Chemicals, Gibbstown N.J.), BL21™ (New England Biolabs, Ipswich, Mass.), SHUFFLE™ (New England Biolabs, Ipswich, Mass.), ROSSETTA™ (Novagen, EMD Chemicals, Gibbstown N.J.) and C43™ (Lucigen, Middleton, Wis.) for expression. The SHUFFLE™ strain (New England Biolabs, Ipswich Mass., described in U.S. Pat. No. 6,569,669, incorporated by reference) is engineered to form disulphide bonds in its cytoplasm (Bessette, P. H. et al. (1999) Proc. Natl. Acad. Sci. USA, 96, 13703-13708). It was found that the *E. coli* SHUFFLE™ strain transfected with SEQ ID NO:5 gave better cell growth and soluble protein expression in non-animal based media and was therefore selected as the host strain.

Example 4

To produce laboratory grade protein product, bacteria carrying the expression construct was grown in a number of media that do not contain animal-derived products. Several non-animal derived media (including APS-SELECT™ (BD, Sparks, Md.), HYPERBROTH™ (AthenaES, Baltimore Md.), and PHYTONE™ (BD, Sparks, Md.) containing Superbroth were tested for expression of the CS/D protein in a Shuffle™ clone (a CS/D clone). A preferred expression medium contained: Phytone™ 10 g/L, Yeast Extract 5 g/L, Magnesium Sulfate heptahydrate 0.24 g/L, Ammonium Sulfate 3.3 g/L, Monobasic Potassium Phosphate 6.8 g/L, Sodium Phosphate Dibasic 7.1 g/L, Glycerol 5 ml/L, Dextrose 0.5 g/L and Kanamycin 0.1 g/L.

Typically in the laboratory, CS/D clone was grown for 16 hrs in a small volume of media (about 25 ml) at about 37° C. which was then inoculated into 1.5 L in a fermentation tank (New Brunswick Scientific). The fermentation culture was grown for ~6 hrs at about 37° C., pH 6.8 and 400 rpm agitation to a final optical density at about 600 nm of ~6 to 7 AU. The culture was induced using 0.5 mM IPTG for 2 hrs, and the final bacterial cell pellet was harvested by centrifugation and stored at about −70° C.

In the laboratory, CS/D protein was purified from the bacterial cell pellet using 3 chromatographic steps, first was a Ni-affinity column (Qiagen), the second was a Q-sepharose anion exchange column (GE Healthcare) and the third was gel-filtration using a Superdex-75 column (GE Healthcare). A typical lab-scale purification was initiated by resuspending 10 g of bacterial cell paste in a resuspension buffer (20 mM Phosphate buffer+450 mM NaCl+0.5% Sarkosyl (pH=7.2)) and lysing by microfluidization. The lysate was then cleared by centrifugation, diluted five-fold in 20 mM Phosphate buffer+450 mM NaCl (pH=7.2) and loaded on 15 ml Ni—NTA Superflow matrix (Qiagen) column mounted on a AKTA Purifier FPLC system (GE Healthcare). The column was washed with 120 ml of wash buffer-1 (20 mM Phosphate buffer+450 mM NaCl+0.1% Sarkosyl+20 mM imidazole, pH=7.2) followed by 120 ml of wash buffer-2 (75 mM Tris, pH 9.0). Protein was eluted from the Ni column using Ni-elution buffer (500 mM imidazole, 75 mM Tris, pH 9.0).

The elution from the Ni-column was diluted five-fold in Q-dilution buffer (75 mM Tris, pH 9.0) and loaded on a packed 3 ml Q-sepharose column. The column was washed with 10 volumes of the Q-dilution buffer. Protein from the Q column was eluted using a linear gradient of 100% Q-dilution buffer to 100% Q-gradient buffer (75 mM Sodium Phosphate monobasic, pH 5.0). The major peak of the protein was collected and analyzed by SDS-PAGE.

The major protein peak of the Q column was purified further by loading on to Superdex-75 gel-filtration matrix (GE Healthcare) packed in a Vantage L Laboratory Column (Millipore). The column was pre-equilibrated in phosphate buffered saline (pH=7.2). The protein peak was monitored, collected and analyzed on SDS-PAGE.

Figure 7:
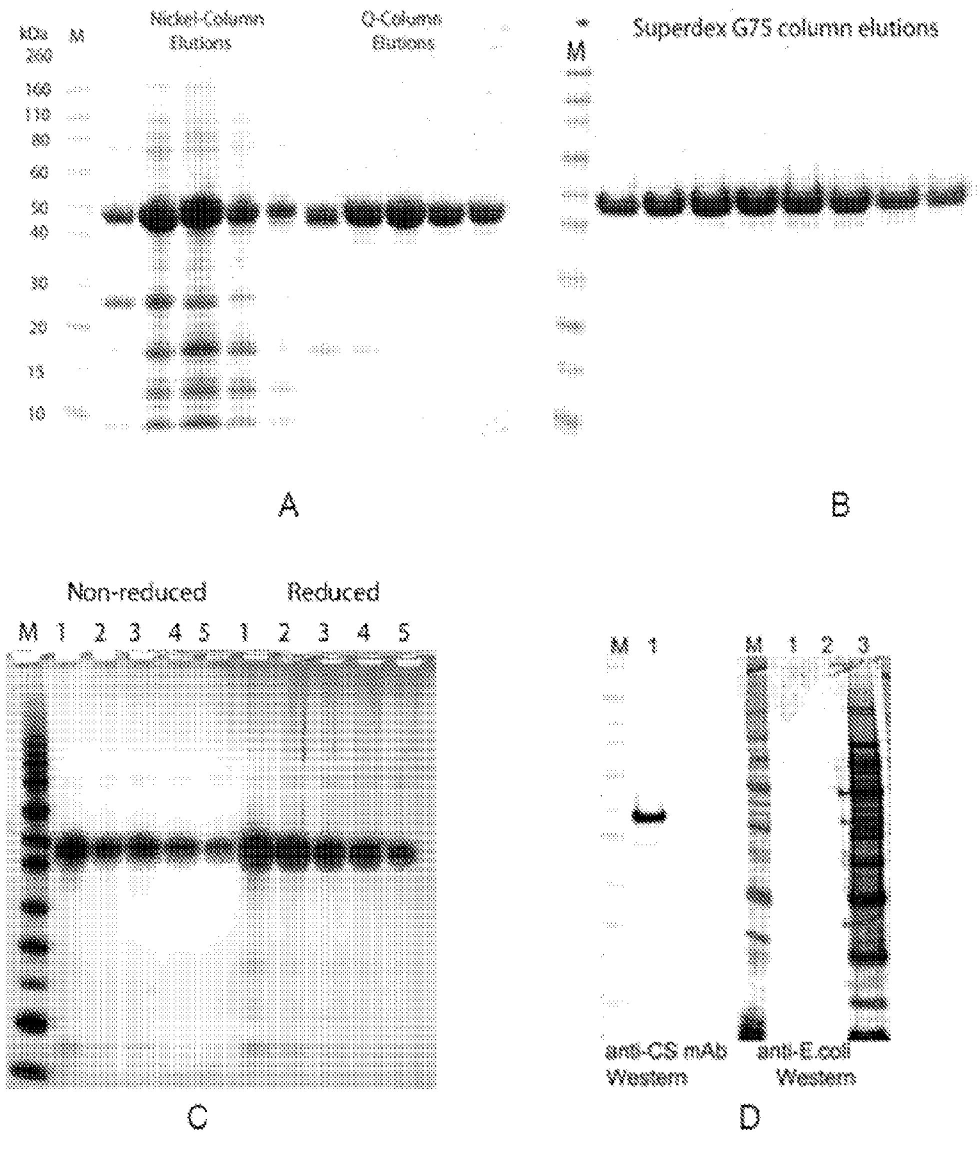
FIGS. 7A, 7B, 7C, and 7D depict the results of purity and identity studies on a laboratory grade CS/D protein.

FIG. 7 shows the results from the step-wise purification of CS/D protein over 3 chromatographic columns. Starting with 10 g bacterial paste, CS/D protein was purified to ~60% purity following the Ni~NTA chromatography step (FIG. 7A, Ni column elutions). A second step of purification on the anion exchange column resulted in ~90% pure product (FIG. 7A, Q-column elutions). The major protein peak from the Q column was then loaded on a Superdex™-75 column, resulting in >95% pure protein (FIG. 7B). The protein was highly purified as evidenced by Silver staining (FIG. 7C). The CS/D protein band migrated as a tight band monomer under non-reducing and reducing conditions, with a slight mobility difference, indicating the presence of reduction sensitive disulphide bonds (FIG. 7C). The protein was recognized by a CSP specific mAb (FIG. 7D, western). On a western blot using polyclonal anti-sera against host cell *E. coli* proteins (FIG. 7D, right panel), no *E. coli* specific bands were detected in the purified CS/D product (FIG. 7D, lanes 1 and 2), establishing the identity and purity of the CS/D product. The final product had an endotoxin content of 0.5 EU/microgram protein as measured by chromogenic *Limulus* amebocyte lysate (LAL)

endpoint assay (Associates of Cape Cod, Falmouth Mass.), which is acceptable for human-use.

Example 5

In this Example, the immunogenicity of the laboratory produced recombinant Pf CS/D protein is shown. 2.5 micrograms of recombinant CS/D protein was combined with Montanide ISA 720 adjuvant (Seppic, Fairfield N.J.) or a control composition containing PBS and Montanide was used to vaccinate ten C57BL6 mice three times on days 0, 14, and 30. The vaccines were given via intraperitoneal injection. The sera from the vaccinated mice was collected two weeks after the second and third dose and tested by ELISA to determine the level of anti-CSP antibody response. FIG. 8A shows the mice exhibited a strong antibody response following the $2^{nd}$ and $3^{rd}$ doses of the vaccine. Ten control mice vaccinated with PBS+Montanide showed no anti-CS antibodies.

Two weeks after the third dose, when the ELISA titer was maximal, ten CS/D vaccinated mice and ten control group mice that had received a PBS+Montanide ISA720 composition were challenged with a transgenic rodent malaria parasite *P. berghei* expressing a functional *P. falciparum* CSP gene (Pb—Pf transgenic) (Tewari, R., R. Spaccapelo, et al. (2002). The mice were challenged with about 15,000 infective Pb—Pf transgenic sporozoites via intravenous tail vein injection. Appearance of blood stage parasites was monitored by daily giemsa staining (Fischer Scientific) for 15 days. Following challenge, none of the control mice were protected (all became slide-positive by day 7 post challenge), while eight of ten CS/D vaccinated mice showed sterile protection as indicated by no blood stage parasitemia (only two of the ten mice showed parasitemia by day 9; see FIG. 8B). The sera from these mice showed reactivity with CSP on the surface of methanol fixed sporozoites by an immuno-fluorescence assay (FIG. 8C). These data lend support to the vaccine candidacy of the CS/D protein as a future malaria vaccine. The laboratory grade CS/D vaccine therefore had an efficacy of 80% against malaria challenge in this rodent malaria experiment model.

Example 6

Figure 9:
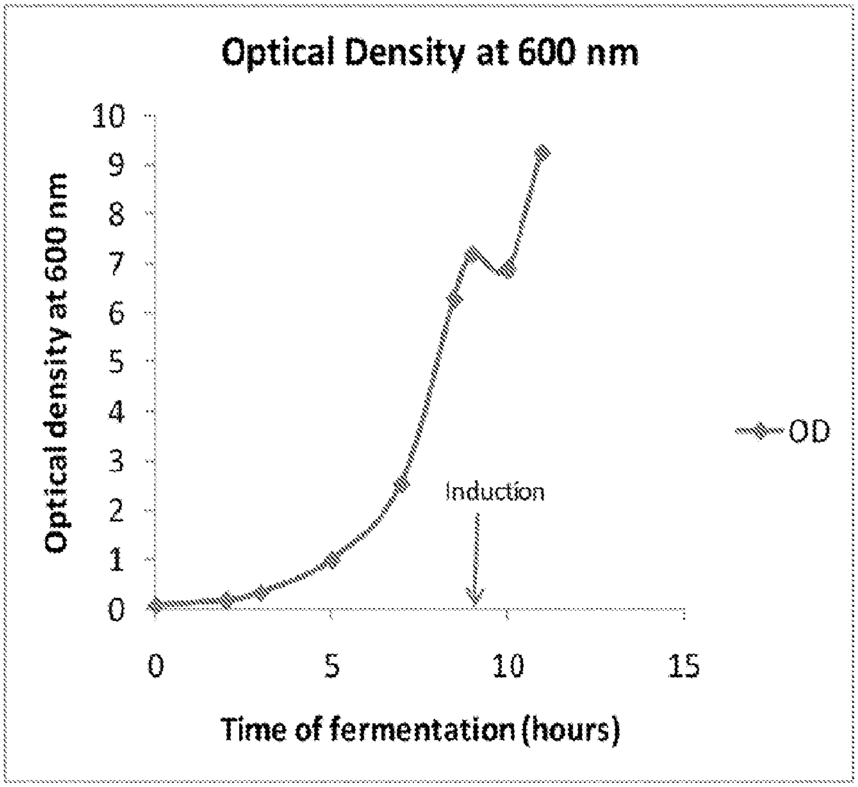
FIG. 9 depicts the growth curve of bacteria containing a CSP construct in a 300 L fermentor produced under cGMP environment at the Bioproduction facility at the Walter Reed Army Institute of Research, Silver Spring, Md.

In this Example, a method using current Good Manufacturing Practice (cGMP, as found in CFR 21) for the manufacture of soluble rCSP protein in animal-free media for vaccine use is demonstrated. cGMP are required for the production of injectables for humans to produce substantially pure protein preparations. A procedure to produce large quantities of vaccine grade soluble protein was developed. First, a cell bank for the *E. coli* containing a nucleotide encoding the recombinant CS/D protein (CS/D#9-pETK-Shuffle) was established. The procedure involved inoculating one baffled 500 ml Erlenmeyer flask containing 120 ml of Growth Medium (1.2 g Phytone, 0.6 g Yeast Extract, 0.029 g $MgSO_4$ 0.39 g ammonium sulfate, 0.81 g Potassium Phosphate Monobasic, 0.84 g Sodium Phosphate Monobasic supplemented with 30 μg/ml Kanamycin sulfate and 1% Dextrose) with the CS/D#9-pETK-Shuffle bacteria stock. The culture was grown at 37±1° C. until an OD of 1.0 at 600 nm was obtained. Glycerol was then added to the culture as a cryopreservative to a final concentration of 15% (v/v). The culture was aliquoted into cryovials at 1.0 ml per vial and placed in controlled storage at about −70° C. for long term storage. The final product (cell bank vials) met all of the criteria set in compliance with the cGMP (CFR 21), which included sterility of the medium at the beginning of the experiment and formation of cream colored colonies when cells were plated on a agar plate. Restriction digestion of DNA miniprep from the bacterial stock, confirmed that the plasmid was present in the frozen bacteria. The above process resulted in 100 vials of a Production Cell Bank of CS/D expressing bacterial cells. For the fermentation of CS/D clone at 300 L scale in compliance with the cGMP, the procedure involved thawing a Production Seed vial (stored at about −80±10° C.), and inoculating 0.9 ml of this stock into 3 L growth medium (30 g Phytone, 15 g Yeast Extract, 9.9 g Ammonium Sulfate, 20.4 g Potassium phosphate monobasic, 21.3 g Sodium phosphate dibasic, 0.73 g $MgSO_4$, 15 ml glycerol, 30 g Dextrose, 0.11 g Kanamycin, pH adjusted to 6.8). The OD of this starter culture reached 3.92 after 12 hours of incubation at 32° C. and 150 rpm agitation. This 3 L starter culture was used to inoculate the fermenter containing 300 L of a growth medium containing 3 kg Phytone, 1.5 kg Yeast Extract, 990 g Ammonium sulfate, 2.04 kg potassium phosphate monobasic, 2.13 kg Sodium phosphate dibasic 73.5 g Magnesium sulfate, 1.5 L glycerol (animal free), 30 ml antifoam, 750 g Dextrose, 11.5 g Kanamycin sulfate, pH adjusted to 6.8. The culture is grown at 28° C., 400 rpm agitation, 299 L/min airflow and 2.3 psig pressure and the pH was maintained at about 6.8 using 1N NaOH and 1N phosphoric acid (growth curve is shown in FIG. 9). After the culture reached an OD of 7.2, it was induced with 0.5 mM IPTG for 2 hours.

Approximately 4 kg of cell paste was harvested by continuous flow centrifugation and stored frozen at about −80±10° C. The fermentation culture conditions were in compliance with cGMP, including the sterility of the starting culture media and formation of cream colored colonies by the bacteria plated on agar plate. The viability of the culture was $2.2\times10^9$ cfu/ml, with only gram negative rods observed during microscopic examination.

For large scale purification of soluble protein, under GMP conditions, the following buffers were prepared.

1. 2×20 L of "Buffer A"—The Lysis and Nickel NTA Equilibration Buffer: 15 mM Sodium Phosphate, 5 mM Potassium Phosphate, 450 mM Sodium Chloride, 20 mM Imidazole (pH 7.4).

2. 20 L of "Buffer B"—Nickel NTA Wash 1 Buffer: 5 mM Sodium Phosphate, 5 mM Potassium Phosphate, 450 mM Sodium Chloride, 20 mM Imidazole, 1.0% Sarcosyl, pH 6.0).

3. 20 L of "Buffer C"—Nickel NTA Wash 2 Buffer: 15 mM Sodium Phosphate, 5 mM Potassium Phosphate, 450 mM Sodium Chloride, 20 mM Imidazole, 1.0% Triton X-100 (pH 6.0).

4. 20 L of "Buffer D"—Ni—NTA Wash 3: 75 mM Tris, 35 mM Imidazole (pH 9.1).

5. 10 L of "Buffer E"—Ni—NTA Elution Buffer (75 mM Tris, 250 mM Imidazole (pH 9.1).

6. 20 L of "Buffer F"—Q Equilibration and Wash Buffer: 75 mM Tris (pH 9.1).

7. 10 L of "Buffer G"—Q Sepharose Wash 2: 75 mM Tris, 40 mM Sodium Chloride (pH 9.1).

8. 10 L of "Buffer H"—Q Wash −3: 10.7 mM Sodium Phosphate, 2.5 mM Potassium Phosphate (pH 9.1).

9. 5 L of "Buffer I"—Q Sepharose Elution Buffer: 7.5 mM Sodium Phosphate, 2.5 mM Potassium Phosphate, 20 mM NaCl (pH 7.0).

10. 2×20 L of "Buffer M,"—Column Sanitization Solution: 0.2 N NaOH.

11. 10 Liters of "Solution O"—Q Regeneration Buffer: 10 mM Sodium Phosphate, 260 mM Sodium Chloride (pH 6.5).

12. Nickel-Nitrile-Triacetic Acid (Ni—NTA) Superflow Column: 1018 ml packed and equilibrated in "buffer A".

13. Q Sepharose Column: 450 ml packed and sanitized with 5 column volumes (CV) of "Solution M, followed by 10 CV of water, 3 CV of "buffer O" and equilibrated in "buffer F".

The following procedure was used for cGMP compliant protein purification.

Figure 10:
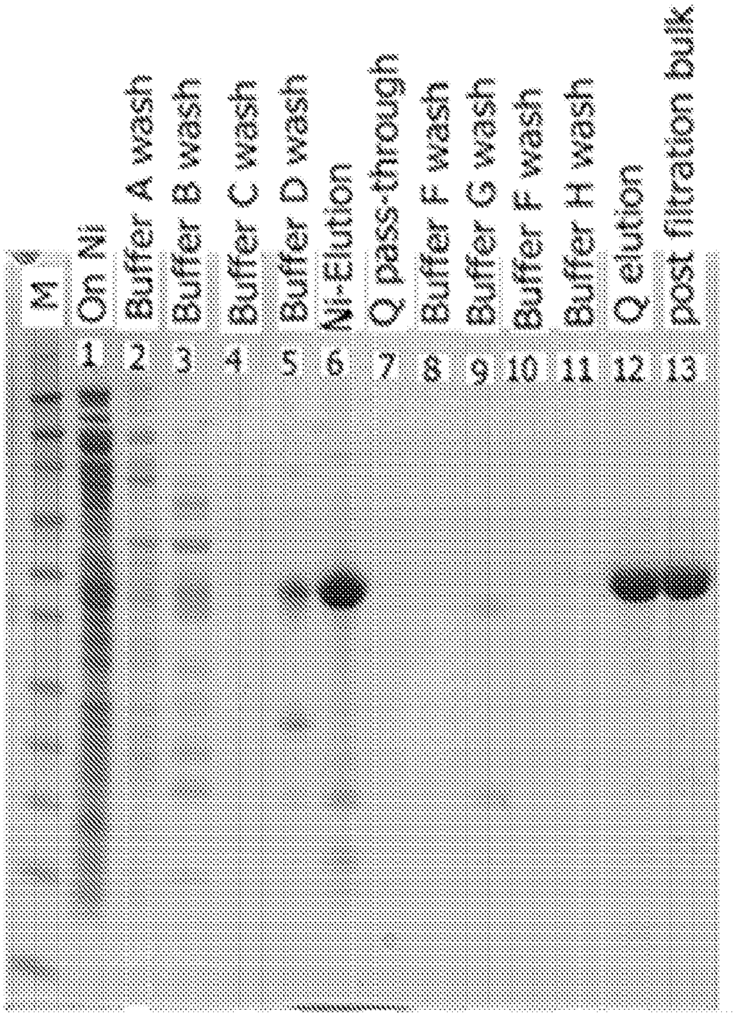
FIG. 10 depicts SDS-PAGE analysis using coomassie blue staining of samples collected during the cGMP compliant purification process of the present technology, including protein that was loaded on the Ni column (lane 1), wash samples with buffer A (lane 2), wash samples with buffer B (lane 3), wash samples with buffer C (lane 4), wash samples with buffer D (lane 5), elution sample from Ni column (lane 6), sample that flowed through Q column (lane 7), buffer wash F (lane 8), buffer wash G (lane 9), buffer wash F (lane 10), buffer wash H (lane 11), sample eluted from Q column (lane 12) and post filtration CS/D bulk (lane 13).

Day 1: A total of 1.5 Kg of frozen wet cell paste from the −80° C. storage was placed into a 2-8° C. refrigerator overnight for thawing. On day 1, about 12 L of chilled "Buffer A" (Lysis Buffer) was added to the thawed cell paste (8 ml of solution A was added per gram of cell paste). The cell paste was stirred using a Turrax homogenizer on wet ice for 20 min, and the final temperature of the cell suspension was about 6.9° C. The bacterial suspension was lysed by running through a microfluidizer, and the final temperature of the lysate was about 7.6° C. Following lysis, the solution was cleared by centrifugation in a Sorvall high speed centrifuge at 14,500 RPM, for 60 minutes (temperature set to about 2-8° C.). A total of 12.6 L of supernatant was decanted and loaded on to a 980 ml packed volume Ni—NTA column at the rate of 100 ml/min. This Ni load sample was analyzed by SDS-PAGE as shown in FIG. 10, lane 1. The column was then washed with 11 L "Buffer A" at 190 ml/ml flow rate (FIG. 10, lane 2), followed by 11 L of "Buffer B", at 210 ml/ml (FIG. 10, lane 3) and 13.5 L "Buffer C" at 175 ml/min (FIG. 10, lane 4). The column was stored at about 4° C. overnight in "Buffer C".

Day 2: The Ni column was washed with about 9.2 L "Buffer D" at 142 ml/min (FIG. 10, lane 5) and the protein was eluted from the Ni-column in 2 L of "Buffer E" at 140 ml/min flow-rate. The OD of the Ni-elutate pool was 1.136 (FIG. 10, lane 6). The protein elution from the Ni column was diluted 1:2 in "Buffer E" to a final OD of 0.5 and was stored overnight at about 4° C.

Day 3: The 4 L diluted Ni—NTA elution was loaded on a 486 ml Q Sepharose column at 84 ml/min. The column was pre-equilibrated in Buffer F. The Q column was washed with 5.5 L of "Buffer F" at 79 ml/min (FIG. 10, lane 8), followed by 5.5 L of "Buffer G" at 82 ml/min (FIG. 10, lane 9), and again with 2 L of "Buffer F" at 82 ml/min (FIG. 10, lane 10), followed by 2 L of "Buffer H" at 82 ml/min (FIG. 10, lane 11) and the final product was eluted from the Q Sepharose column in 1500 ml "Buffer I" at 82 ml/min flow-rate (FIG. 10, lane 12). The fractions containing the protein were pooled (1.5 L) and optical density at 280 nm showed the OD was 0.96. The protein was then diluted to an OD of about 0.4, final volume 3.57 L, which amounted to 1,775 micrograms of CS/D soluble protein.

Day 4: The protein was filtered through a 0.2 micron cellulose acetate filter and frozen down at about −70° C. as purified bulk soluble CS/D protein (FIG. 10, lane 13).

Figure 11:
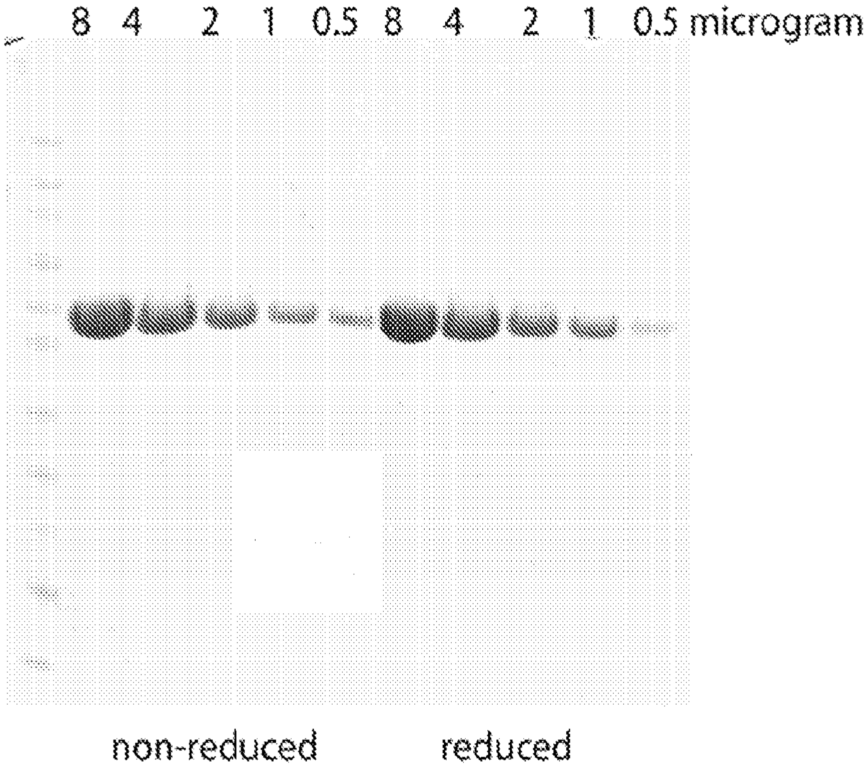
FIG. 11 depicts the purity of a sample of purified soluble protein run under non-reduced and reduced conditions on SDS-PAGE by Coomassie blue staining.

The purity and stability of the cGMP grade CS/D protein was characterized as follows. Evidence of CS/D protein homogeneity was detected by coomassie blue stained SDS-PAGE, with samples run under non-reduced and reduced conditions (FIG. 11). Note that up to 8 micrograms of cGMP grade protein was loaded to check for product purity.

Figure 12:
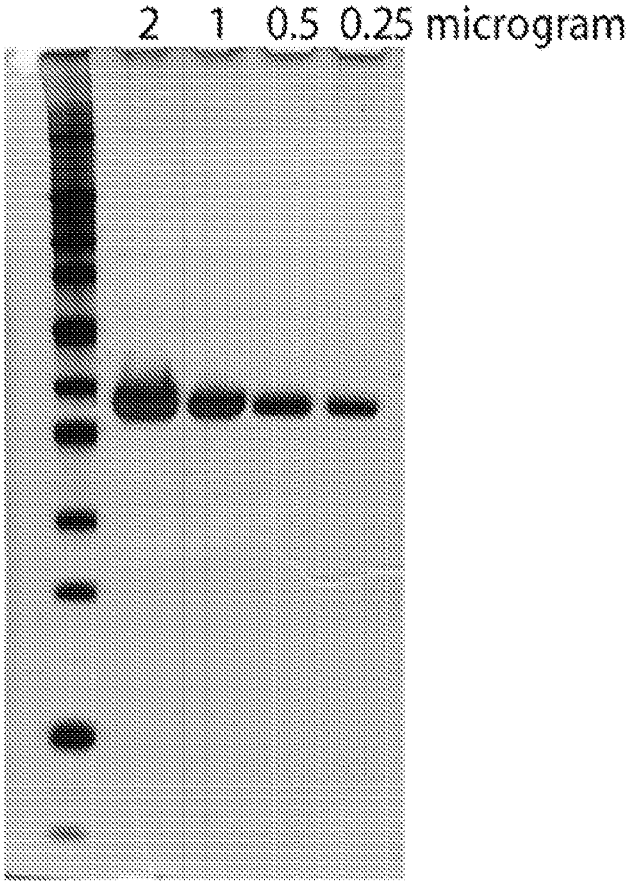
FIG. 12 depicts the purity of the cGMP compliant purified protein using silver staining under reducing conditions.

Silver stained bulk purified CS/D protein was also analyzed under reducing condition, and it also showed a highly purified product, as demonstrated in FIG. 12. Note that up to 2 microgram protein was loaded to check for purity (FIG. 12).

TABLE 1

| Sample | Test | Specification | Result | Pass/ Fail |
|---|---|---|---|---|
| Purified Bulk | Bulk Lot Evaluation | Homogenous clear, colorless liquid | Clear, colorless | PASS |
| Purified Bulk | Sterility | No growth | No growth | PASS |
| Purified Bulk | pH | 6.9-7.5 | 7.3 | PASS |
| Purified Bulk | Protein Content by BCA | Report as Tested 400 μg/ml | 418.9 μg/ml | PASS |
| Purified Bulk | Identity by SDS-PAGE (reduced) | Report as Tested Molecular weight between 35-50 kDa | ~40 kDa | PASS |
| Purified Bulk | Rabbit Pyrogen | Non-pyrogenic | Non pyrogenic | PASS |
| Purified Bulk | Purity by SDS-PAGE | Purity >90% | >99% | PASS |

Table 1 demonstrates a summary of the testing and results of the purified bulk CS/D protein expressed and purified by the above-described cGMP method. The purified protein fulfills and exceeds the requirements for a human-grade vaccine injectable.

Host cell protein (HCP) content of cGMP grade CS/D was measured by ELISA. The cGMP product contained <1 ng/ml of HCP in a 418 microgram per ml protein concentration bulk as measured by Cygnus HCP ELISA. Thus, the product is about >99% pure. No endotoxin was detectable by LAL assay (minimum detection limit is 0.1 EU/ml) or by the Gel-Clot endotoxin assay. The product is suitable as a human-use injectable.

Figure 13:
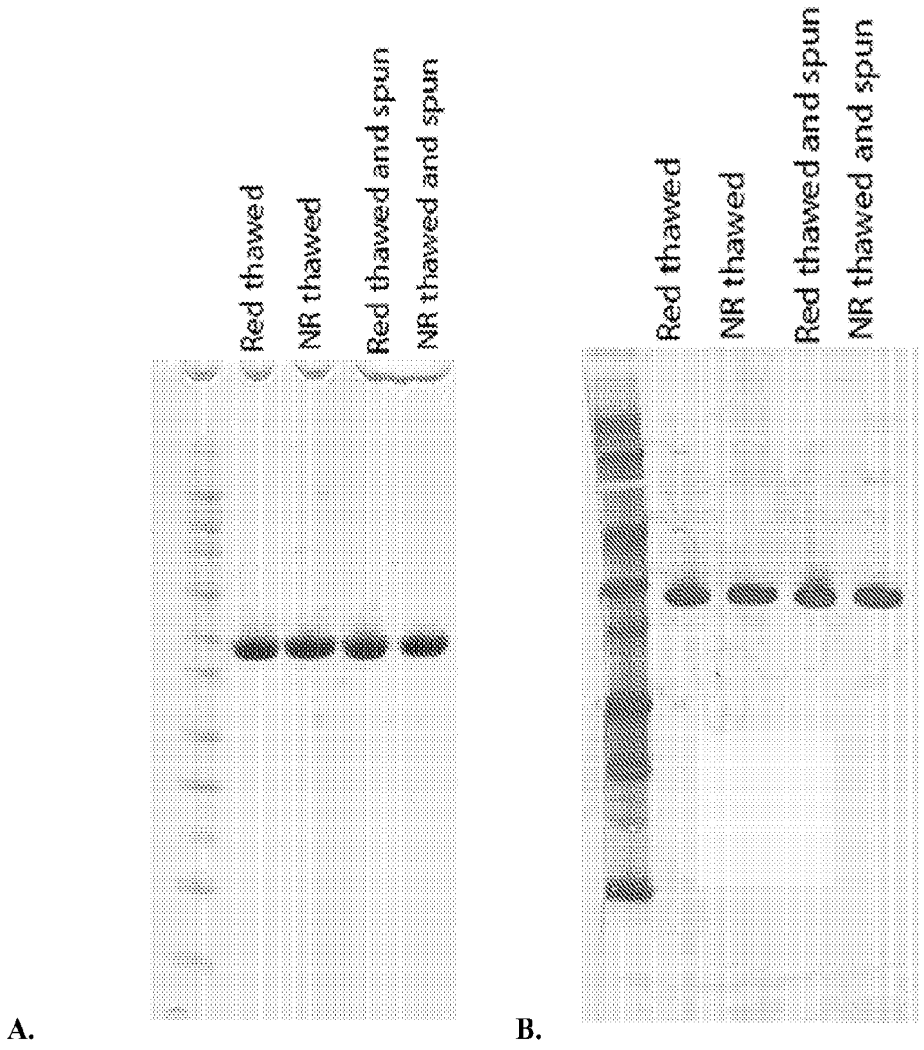
FIGS. 13A and 13B depict the stability of the cGMP grade soluble protein of the present technology during a freeze-thaw cycle. Samples were analyzed after thawing (labeled as 'thawed') and after a spin at 10K for 10 min (labeled as 'thawed and spun') on SDS-PAGE (A) and western blot (B) using anti-CSP antibodies under reduced (Red) or non-reduced (NR) conditions. The anti-CSP antibodies specifically bind to CSP.

Stability of CS/D product during freeze-thaw was determined as follows: The cGMP bulk CS/D protein was thawed and run on a gel under reduced and non-reduced conditions. One way to detect if the protein is unstable in solution is to analyze it on a gel before and after spinning out any precipitated material which can removed by centrifugation. FIG. 13 shows no difference in band intensity in pre and post-spin samples of the bulk protein CS/D freshly thawed and analyzed under reduced or non-reduced conditions. This indicated that no rCSP would be lost to precipitation during the freeze-thaw. It should be noted that western blot is a very sensitive way to detect protein aggregation and we did not see any rCSP smear above the main band.

Figure 14:
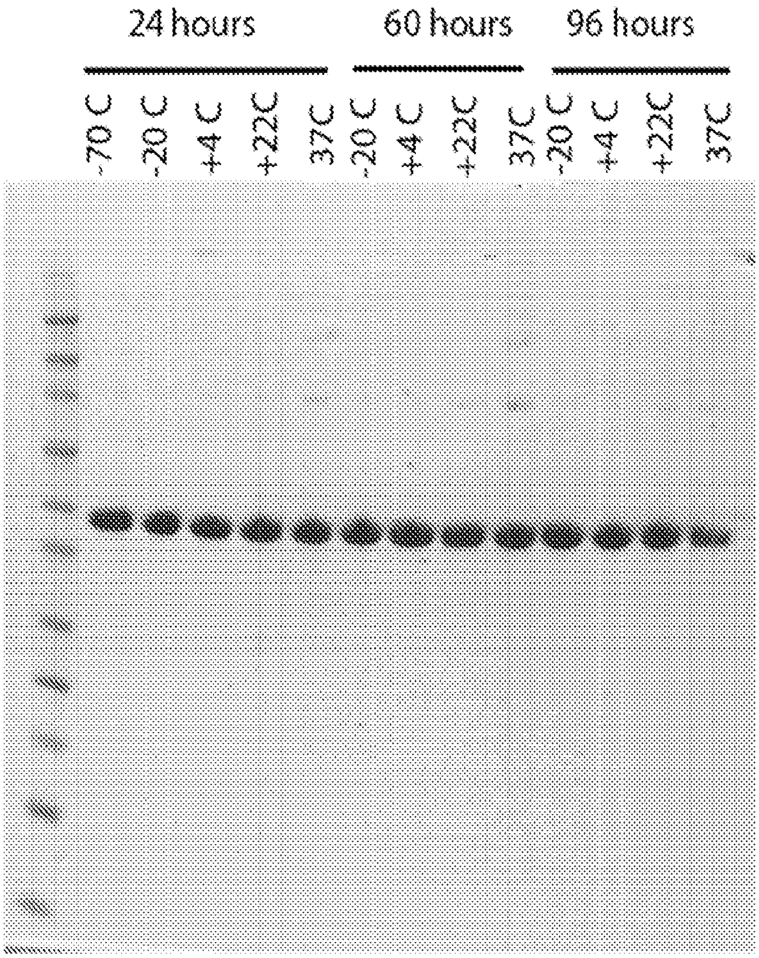
FIG. 14 depicts the thermal stability of cGMP grade CS/D purified soluble protein analyzed by non-reduced coomassie stained SDS-PAGE at four different temperatures and three time points.

Thermal stability of the CS/D product was evaluated as follows. In addition to loss during freeze-thaw, the thermal stability of a CS/D product would be an important characteristic, particularly if additional steps of chemical modification are to be carried out, under an elevated temperature. Thermal stability experiments with the CS/D product were conducted at four different temperatures. It was found that the protein did not degrade or aggregate between −70 to +22° C. incubation for up to 96 hrs as evidenced by non-reduced SDS-PAGE (FIG. 14). At 37° C., some self aggregation was observed (still only distinct bands of multimers were seen and not a smear). Some degradation was also evidenced by reduction in the density of the main band following >60 hr of incubation at 37° C. However, the CS/D product was thermally stable between −70° C. and +22° C.

Figure 15:
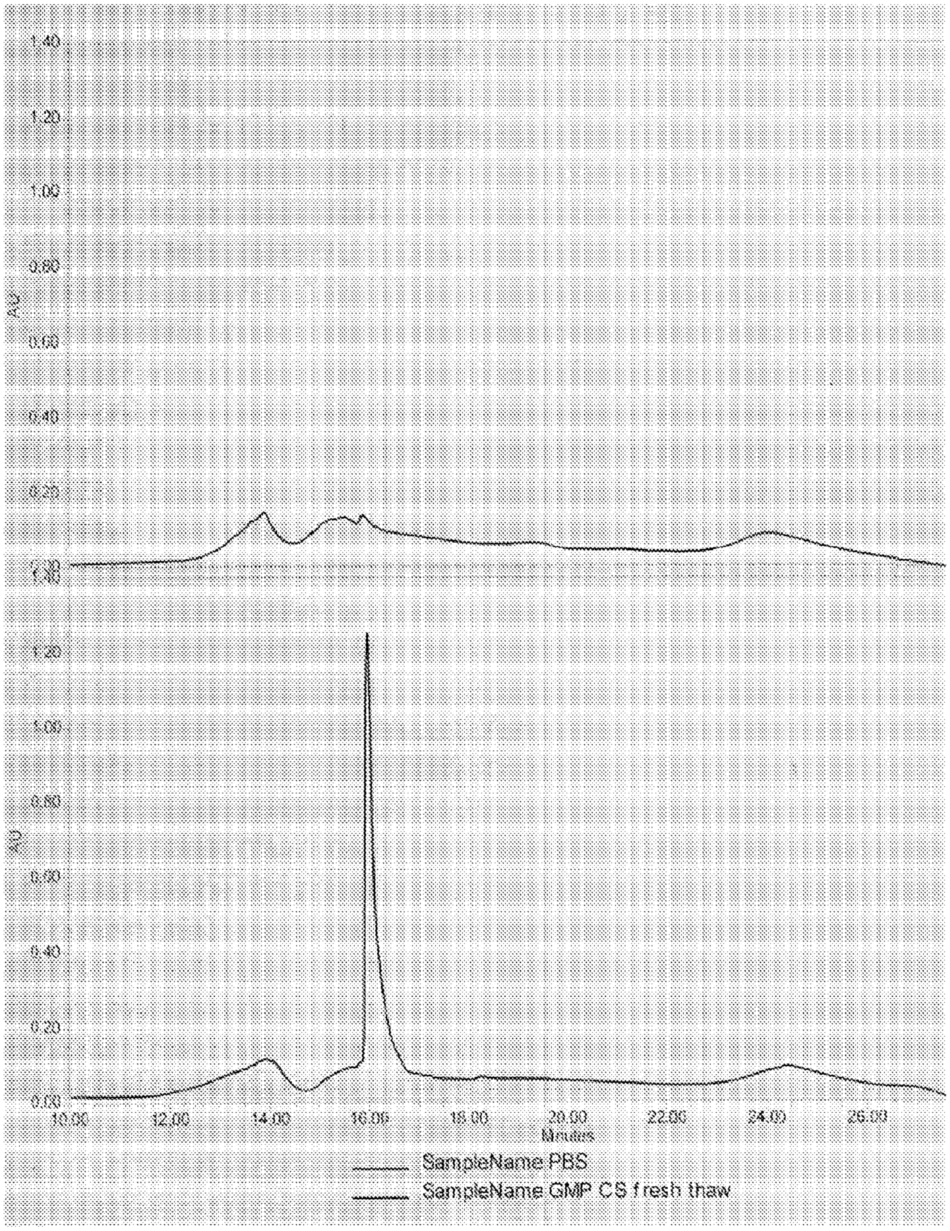
FIG. 15 depicts the reversed-phase HPLC profile of CS/D soluble purified protein.

Reversed Phase HPLC analysis of the cGMP rCSP product was used to assess conformational homogeneity. The CS/D bulk protein was analyzed on a reversed-phase C18 column (Protein and Peptide™ VYDAC) to determine conformational homogeneity in solution. As seen in the elution profile (FIG. 15), the protein eluted as a single peak and all minor peaks were also present in the PBS control run. Hence, the majority of the CS/D product is present in a single conformation in the bulk protein.

Figure 16:
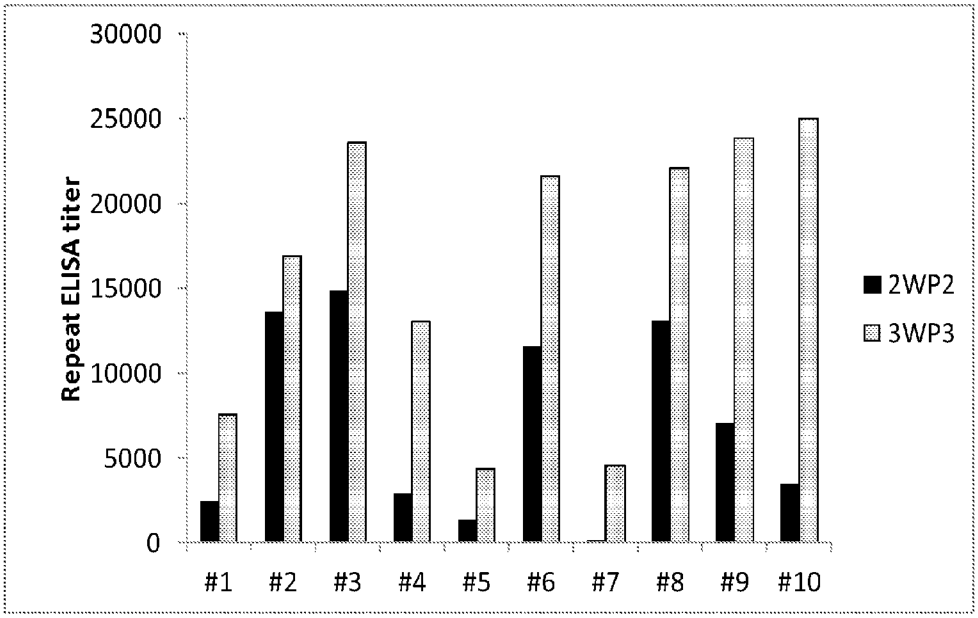
FIG. 16 depicts the antibody titers of individual mice between the second and third boosting doses of the cGMP grade soluble protein of the present technology.
Figure 18:
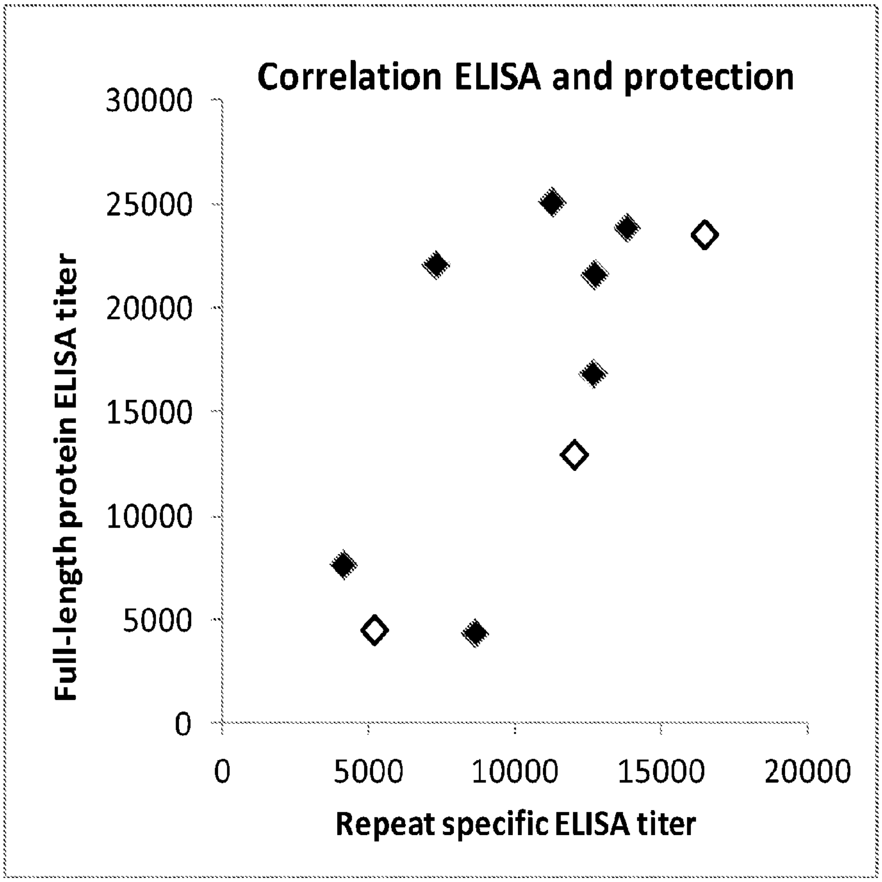
FIG. 18 depicts the correlation between NANP (SEQ ID NO. 13) repeat specific ELISA titer (x axis) and full-length protein ELISA titer (y axis).

Immunogenicity and challenge data with the cGMP CS/D product were determined as follows. The cGMP CS/D protein product was combined with Montanide ISA 720 adjuvant (Seppic, Fairfield N.J.) and vaccinated thrice into ten C57BL6 mice, two weeks apart. Each mouse received 5 micrograms of the antigen and 70 microliters of adjuvant per dose subcutaneously. Control mice received the adjuvant alone in PBS. The sera from the vaccinated mice was collected two weeks after the second and third dose and tested by ELISA. Mice were then challenged with a transgenic strain of *P. berghei* parasites expressing a functional *P. falciparum* CSP gene (Tewari, Spaccapelo et al., 2002). A dose of 2500 transgenic sporozoites was given intravenously, three weeks after the third vaccine dose. All mice that received the CS/D vaccine developed antibodies to the protein as measured by a repeat specific ELISA (FIG. 16). Antibodies were boosted by the third vaccination as seen by higher P3 vs. P2 titers. Seven of 10 CSP vaccinated animals did not become infected following challenge, as evidenced by negative blood smears up to day 12 post challenge. All the adjuvant control mice showed blood stage parasites by day 4 post challenge (FIG. 17B). There was a positive correlation between repeat specific ELISA titers and full-length protein ELISA titers. However all of the protected animals did not have high titer antibodies (FIG. 18). Thus the cGMP grade CS/D vaccine had an efficacy of 70% in this rodent malaria experimental model.

Other embodiments and uses of the invention will be apparent to those skilled in the art from consideration of the specification and practice of the invention disclosed herein. All references cited herein, including all publications, U.S. and foreign patents and patent applications are specifically and entirely incorporated by reference. As used in this specification, the singular forms "a", "an", and "the" include plural reference unless the context clearly dictates otherwise. Thus, for example, a reference to "a recombinant CSP" includes one or more of such circumsporozoite proteins. A reference to "an adjuvant" includes one or more of such adjuvants, and so forth. It is intended that the specification and examples be considered exemplary only with the true scope and spirit of the invention indicated by the following claims. Furthermore, where the term "comprising of" appears, it is contemplated that the terms "consisting of" or "consisting essentially of" could be used in its place to describe certain embodiments of the present technology.

REFERENCES

Blum-Tirouvanziam, U., C. Beghdadi-Rais, et al. (1994). "Elicitation of specific cytotoxic T cells by immunization with malaria soluble synthetic polypeptides." *J Immunol* 153(9): 4134-4141.

Blum-Tirouvanziam, U., C. Servis, et al. (1995). "Localization of HLA-A2.1-restricted T cell epitopes in the circumsporozoite protein of *Plasmodium falciparum." J Immunol* 154(8): 3922-3931.

Coppi, A., C. Pinzon-Ortiz, et al. (2005). "The *Plasmodium* circumsporozoite protein is proteolytically processed during cell invasion." *J Exp Med* 201 (1): 27-33.

Darko, C. A., E. Angov, et al. (2005). "The clinical-grade 42-kilodalton fragment of merozoite surface protein 1 of *Plasmodium falciparum* strain FVO expressed in *Escherichia coli* protects *Aotus nancymai* against challenge with homologous erythrocytic-stage parasites." *Infect Immun* 73(1): 287-297.

Doolan, D. L., H. P. Beck, et al. (1994). "Evidence for limited activation of distinct CD4+ T cell subsets in response to the *Plasmodium falciparum* circumsporozoite protein in Papua New Guinea." *Parasite Immunol* 16(3): 129-136.

Doolan, D. L., R. A. Houghten, et al. (1991). "Location of human cytotoxic T cell epitopes within a polymorphic domain of the *Plasmodium falciparum* circumsporozoite protein." *Int Immunol* 3(6): 511-516.

Doolan, D. L., C. Khamboonruang, et al. (1993). "Cytotoxic T lymphocyte (CTL) low-responsiveness to the *Plasmodium falciparum* circumsporozoite protein in naturally-exposed endemic populations: analysis of human CTL response to most known variants." *Int Immunol* 5(1): 37-46.

Doolan, D. L., A. J. Saul, et al. (1992). "Geographically restricted heterogeneity of the *Plasmodium falciparum* circumsporozoite protein: relevance for vaccine development." *Infect Immun* 60(2): 675-682.

Tewari, R., R. Spaccapelo, et al. (2002). "Function of region I and II adhesive motifs of *Plasmodium falciparum* circumsporozoite protein in sporozoite motility and infectivity." *J Biol Chem* 277(49): 47613-47618.

Tewari, R, D. Rathore et al. (2005) "Motility and infectivity of *Plasmodium berghei* sporozoites expressing avian *Plasmodium gallinaceum* circumsporozoite protein." *Cell Microbiol.* 2005 (5):699-707.

Vaughan, K., M. Blythe, et al. (2009). "Meta-analysis of immune epitope data for all Plasmodia: overview and applications for malarial immunobiology and vaccine-related issues." *Parasite Immunol* 31(2): 78-97.

Zavala, F., A. H. Cochrane, et al. (1983). "Circumsporozoite proteins of malaria parasites contain a single immunodominant region with two or more identical epitopes." *J Exp Med* 157(6): 1947-1957.

Zevering, Y., C. Khamboonruang, et al. (1994). "Life-spans of human T-cell responses to determinants from the circumsporozoite proteins of *Plasmodium falciparum* and *Plasmodium vivax." Proc Natl Acad Sci USA* 91(13): 6118-6122.

The invention claimed is:

1. A soluble recombinant *Plasmodium falciparum* circumsporozoite protein (rCSP) comprising SEQ ID NO:2, or an rCSP of 278 amino acids in length having 95% sequence identity to SEQ ID NO:2.

2. The recombinant *P. falciparum* CSP of claim 1, wherein the rCSP lacks $Met_1$ to $Cys_{25}$ of the N-terminal region of native *P. falciparum* circumsporozoite protein.

3. The recombinant *P. falciparum* CSP of claim 1, wherein the rCSP has 18 or 19 NANP (SEQ ID NO: 13) repeats.

4. The recombinant *P. falciparum* CSP of claim 3, wherein the rCSP has 19 NANP (SEQ ID NO: 13) repeats.

5. The recombinant *P. falciparum* CSP of claim 1, wherein the rCSP has a 0 to 3 NVDP (SEQ ID NO: 14) repeats.

6. The recombinant *P. falciparum* CSP of claim 5, wherein the rCSP has 3 NVDP (SEQ ID NO: 14) repeats.

7. The recombinant *P. falciparum* CSP of claim 1, wherein the rCSP has a C-terminal region that lacks ten to fourteen C-terminus amino acid residues of native *P. falciparum* circumsporozoite protein.

8. The recombinant *P. falciparum* CSP of claim 7, wherein the rCSP ends at a serine.

9. The recombinant *P. falciparum* CSP of claim 1, wherein the rCSP comprises SEQ ID NO:8.

10. A process of producing a soluble recombinant *P. falciparum* CSP, comprising the steps of:

providing *E. coli* cells containing a nucleotide sequence that expresses a recombinant *P. falciparum* CSP according to claim 1;

inducing expression of the recombinant *P. falciparum* CSP in the *E. coli* cells;

lysing the *E. coli* cells to produce *E. coli* lysate;

purifying the recombinant *P. falciparum* CSP from the supernatant of the *E. coli* lysate without denaturing and refolding the recombinant *P. falciparum* CSP.

11. The process of claim 10, wherein the *E. coli* is cultured in media substantially free of components derived from animals.

12. The process of claim 11, wherein the media comprises a combination of ingredients including Phytone, yeast extract, ammonium sulfate, potassium phosphate monobasic, sodium phosphate dibasic, $MgSO_4$, glycerol, dextrose and kanamycin.

13. The process of claim 10, wherein the recombinant *P. falciparum* CSP comprises one or more histidine tags at one or both ends, and wherein the purification step consists essentially of:

purifying the soluble protein over a nickel affinity column; and purifying the soluble protein over a Q-sepharose anion exchange column and recovering a purified protein, wherein the purification step does not include any other chromatographic separation.

14. The process of claim 10, further comprising the step of filtering the purified protein.

15. The process of claim 10, wherein the purified protein is at least about 90% pure recombinant *P. falciparum* CSP as measured by gel densitometry.

16. The process of claim 15, wherein the purified protein is at least about 95% pure recombinant *P. falciparum* CSP as measured by gel densitometry.

17. The process of claim 10, the purified protein comprises less than 1 ng/ml of *E. coli* host proteins.

18. The process of claim 10, wherein the purified protein comprises less than about 5 endotoxin units per microgram protein.

19. The soluble recombinant *P. falciparum* CSP of claim 1, wherein the protein has greater solubility when expressed in *E. coli* than wildtype CSP.

20. The soluble recombinant *P. falciparum* CSP of claim 1, wherein the protein is at least 95% pure as measured by gel densitometry.

21. The soluble recombinant *P. falciparum* CSP of claim 1, wherein the purified protein comprises less than about 5 endotoxin units per microgram protein.

* * * * *